(12) United States Patent
Hsu et al.

(10) Patent No.: US 12,029,817 B2
(45) Date of Patent: Jul. 9, 2024

(54) METHOD FOR MANUFACTURING WATER-IN-OIL-IN-WATER MULTIPLE EMULSION

(71) Applicant: FOOD INDUSTRY RESEARCH AND DEVELOPMENT INSTITUTE, Hsinchu (TW)

(72) Inventors: Chia-Chen Hsu, Hsinchu (TW); Nai-Yi Wang, Hsinchu (TW); Yu-Chen Cheng, Hsinchu (TW); Jinn-Tsyy Lai, Hsinchu (TW)

(73) Assignee: FOOD INDUSTRY RESEARCH AND DEVELOPMENT INSTITUTE, Hsinchu (TW)

( * ) Notice: Subject to any disclaimer, the term of this patent is extended or adjusted under 35 U.S.C. 154(b) by 378 days.

(21) Appl. No.: 17/222,022

(22) Filed: Apr. 5, 2021

(65) Prior Publication Data
US 2021/0393710 A1 Dec. 23, 2021

(30) Foreign Application Priority Data
Jun. 17, 2020 (TW) ................................ 109120452

(51) Int. Cl.
| A61K 9/113 | (2006.01) |
| A61K 9/16 | (2006.01) |
| A61K 35/745 | (2015.01) |
| A61K 35/747 | (2015.01) |
| A61K 47/36 | (2006.01) |
| A61K 47/38 | (2006.01) |
| A61K 47/42 | (2017.01) |
| A61K 47/44 | (2017.01) |
| A61P 1/14 | (2006.01) |

(52) U.S. Cl.
CPC ............... *A61K 9/113* (2013.01); *A61K 9/16* (2013.01); *A61K 35/745* (2013.01); *A61K 35/747* (2013.01); *A61K 47/36* (2013.01); *A61K 47/38* (2013.01); *A61K 47/42* (2013.01); *A61K 47/44* (2013.01); *A61P 1/14* (2018.01)

(58) Field of Classification Search
None
See application file for complete search history.

(56) References Cited

U.S. PATENT DOCUMENTS

| 6,905,717 | B2 | 6/2005 | Beck nee Trescol et al. |
| 8,168,225 | B2 | 5/2012 | Casaña Giner et al. |
| 9,296,987 | B2 | 3/2016 | Chung |
| 9,788,563 | B2 | 10/2017 | Fang et al. |
| 2008/0299200 | A1* | 12/2008 | Leser ............ C09K 23/16 426/534 |
| 2011/0189298 | A1 | 8/2011 | Vos et al. |
| 2012/0039956 | A1 | 2/2012 | Harel et al. |
| 2012/0135017 | A1 | 5/2012 | Harel et al. |
| 2012/0322663 | A1 | 12/2012 | Harel et al. |
| 2015/0031544 | A1 | 1/2015 | Harel et al. |
| 2019/0194259 | A1 | 6/2019 | Harel et al. |

FOREIGN PATENT DOCUMENTS

| CN | 101856604 | A | 10/2010 | |
| CN | 101683604 | B | 1/2012 | |
| CN | 101724589 | B | 5/2012 | |
| CN | 102725393 | A | 10/2012 | |
| CN | 103140145 | A | 6/2013 | |
| CN | 103223164 | B | 8/2014 | |
| CN | 104398478 | B | 5/2017 | |
| CN | 106987525 | A | 7/2017 | |
| CN | 108853021 | A * | 11/2018 | .......... A61K 35/741 |
| CN | 108853021 | A | 11/2018 | |
| CN | 111035013 | A * | 4/2020 | |
| JP | S60199833 | A | 10/1985 | |
| JP | S60184366 | U | 12/1985 | |
| JP | S62220186 | A | 9/1987 | |
| JP | H10179145 | A | 7/1998 | |
| JP | 2003334062 | A | 11/2003 | |
| JP | 2004528811 | A | 9/2004 | |
| JP | 2005185181 | A | 7/2005 | |
| JP | 2007060919 | A | 3/2007 | |
| JP | 2019103903 | A | 6/2019 | |

OTHER PUBLICATIONS

Office Action issued in corresponding Taiwanese Application No. 109120452, dated Jun. 4, 2021, with English translation, 7 pages provided.

Flores-Andrade et al., "Effect of vacuum on the impregnation of Lactobacillus rhamnosus microcapsules in apple slices using double emulsion", Journal of Food Engineering, vol. 202, Jun. 2017, pp. 18-24.

Bruckner et al., "Investigations into the stabilization of a volatile aroma compound using a combined emulsification and spray drying process", European Food Research and Technology, vol. 226, 2007, pp. 137-146.

Pimentel-González et al., "Encapsulation of Lactobacillus rhamnosus in double emulsions formulated with sweet whey as emulsifier and survival in simulated gastrointestinal conditions", Food Research International, vol. 42, Issue 2, Mar. 2009, pp. 292-297.

Shima et al., "Protection of Lactobacillus acidophilus from bile salts in a model intestinal juice by incorporation into the inner-water phase of a W/O/W emulsion", Food Hydrocolloids, vol. 23, Issue 2, Mar. 2009, pp. 281-285.

(Continued)

*Primary Examiner* — Michelle F. Paguio Frising
(74) *Attorney, Agent, or Firm* — HSML P.C.

(57) ABSTRACT

The present invention provides a method for manufacturing a water-in-oil-in-water multiple emulsion, comprising: (a) mixing an active component with an internal aqueous phase to form a homogenized mixture; (b) mixing the homogenized mixture with an oleaginous phase to form a water-in-oil emulsion; and (c) mixing the water-in-oil emulsion with an external aqueous phase to form the water-in-oil-in-water multiple emulsion, wherein the external aqueous phase comprises water and an excipient, and wherein the excipient comprises a whey protein concentrate and a modified starch.

20 Claims, 25 Drawing Sheets

(56) References Cited

OTHER PUBLICATIONS

Rodriguez-Huezo et al., "Viability of Lactobacillus plantarum entrapped in double emulsion during Oaxaca cheese manufacture, melting and simulated intestinal conditions", LWT—Food Science and Technology, vol. 59, Issue 2, Part 1, Dec. 2014, pp. 768-773.

Hou et al., "Increase of viability of entrapped cells of Lactobacillus delbrueckii ssp. *bulgaricus* in artificial sesame oil emulsions", American Dairy Science Association, Feb. 2003;86, pp. 424-428.

Shima et al., "Protection of Lactobacillus acidophilus from the low pH of a model gastric juice by incorporation in a W/O/W emulsion", Food Hydrocolloids, vol. 20, Issue 8, Dec. 2006, pp. 1164-1169.

Office Action issued in corresponding Japanese Application No. 2021-071059, dated May 24, 2022, with English translation, 5 pages provided.

* cited by examiner

METHOD FOR MANUFACTURING WATER-IN-OIL-IN-WATER MULTIPLE EMULSION

TECHNICAL FIELD

The present invention relates to a method for manufacturing an emulsion, and, particularly, to a method for manufacturing a water-in-oil-in water multiple emulsion.

BACKGROUND

According to the statistical analysis data from the Industry & Technology Intelligence Service (ITIS) of the Food Industry Research and Development Institute (FIRDI), the market for dietary supplements in Taiwan was 54.1 billion NT dollars in 2013, and the market has continued to grow. Among them, *Lactobacillus* bacteria account for 5% of the market, which demonstrates its value to those able to develop improved products utilizing it. The key development targets for new probiotic products are to improve survival rate and stability of during manufacturing and storage, as well as in the gastrointestinal tract.

SUMMARY

The main purpose of the present invention is to provide a method for manufacturing a water-in-oil-in-water multiple emulsion with improved stability of the encapsulated active component.

Hence, the present invention provides a method for manufacturing a water-in-oil-in-water multiple emulsion, which comprises the steps of:
(a) mixing an active component with an internal aqueous phase to form a homogenized mixture;
(b) mixing the homogenized mixture with an oleaginous phase to form a water-in-oil emulsion; and
(c) mixing the water-in-oil emulsion with an external aqueous phase to form the water-in-oil-in-water multiple emulsion,
wherein the external aqueous phase comprises water and an excipient, and wherein the excipient comprises a whey protein concentrate and a modified starch.

The present invention further provides a composition obtained from the aforementioned method.

BRIEF DESCRIPTION OF THE DRAWINGS

FIG. 5A shows the variations of the counts of *Clostridium perfringens* in the feces of mice administered with the test substances over time (Day 3, Day 7, and Day 14).

FIG. 9A shows the variations of the counts of *Clostridium perfringens* in the feces of mice administered with the test substances over time (Pre-Day 1, Day 7, and Day 14).

FIG. 9B shows the effects of the test substances on the amounts of *Clostridium perfringens* in the cecal contents of mice administered with the test substance at the end of the tests (Day 21).

DETAILED DESCRIPTION

Figure 1:
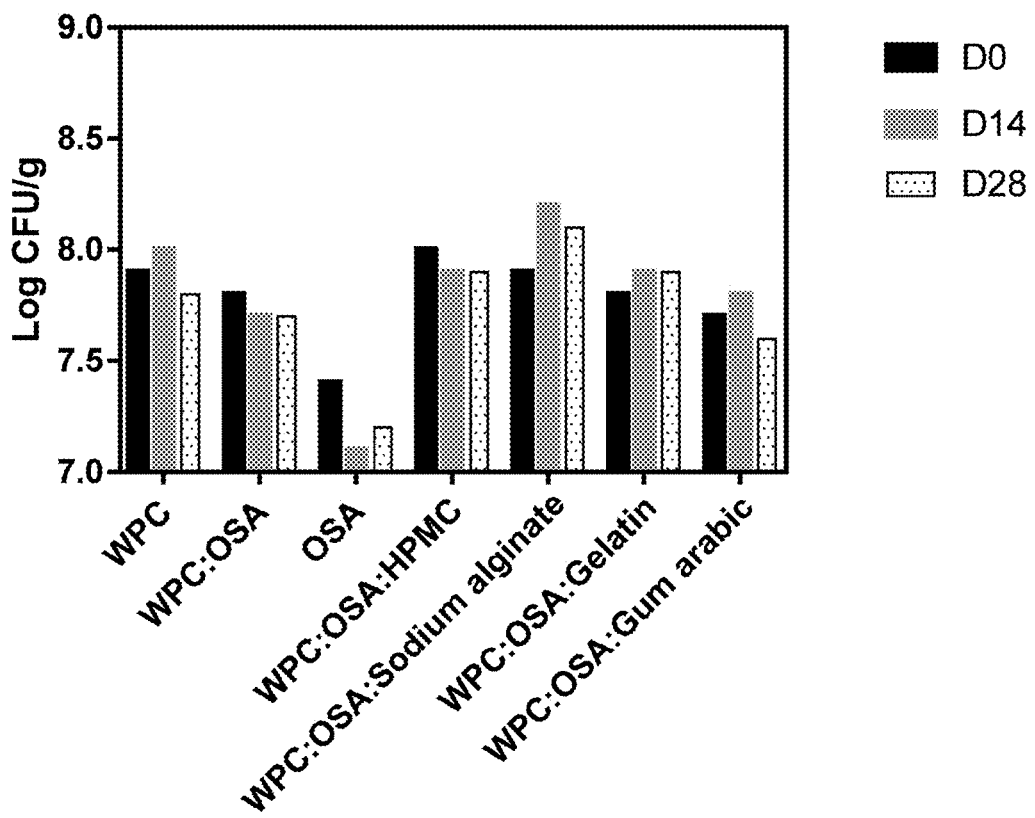
FIG. 1 shows the stability of the *Lactobacillus casei* (*L. casei*) multiple emulsion powders analyzed at 4° C.

The present invention can be more readily understood by reference to the following detailed description of various embodiments of the invention, the examples, and the chemical drawings and tables with their relevant descriptions.

As utilized in accordance with the present disclosure, the following terms, unless otherwise indicated, shall be understood to have the following meaning:

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

The present invention introduces multiple emulsification technology into the development of oral administration products, and establishes encapsulation technology for oral administration products through formula and process designs. The multiple emulsification technology uses a multilayer film structure to create a spatial separation, and the active component is encapsulated in an internal aqueous phase for isolation and protection purposes. The multiple emulsification technology may be utilized in a wide variety of products.

Emulsification technology refers to two phases, which are originally immiscible, and one of which is dispersed as fine particles in the other phase. Emulsions can be classified into oil-in-water (O/W) system and water-in-oil (W/O) system. Multiple emulsion is a complex system in which both W/O emulsion and O/W emulsion exist simultaneously. According to the properties of the dispersed phase and those of the continuous phase, multiple emulsions can be classified into water-in-oil-in-water (W/O/W) system and oil-in-water-in-oil (O/W/O) system. Due to the multilayer film structure, multiple emulsion can encapsulate water-soluble and oil-soluble substances integrally for the purposes of isolation, protection, taste masking, controlled release, etc. Accordingly, multiple emulsion technology has potential for industrial applications.

That is, the present invention provides a method for manufacturing a water-in-oil-in-water multiple emulsion comprising the steps of:
(a) mixing an active component with an internal aqueous phase to form a homogenized mixture;
(b) mixing the homogenized mixture with an oleaginous phase to form a water-in-oil emulsion; and
(c) mixing the water-in-oil emulsion with an external aqueous phase to form the water-in-oil-in-water multiple emulsion, wherein the external aqueous phase comprises water and an excipient, and wherein the excipient comprises a whey protein concentrate and a modified starch.

The water-in-oil-in-water multiple emulsion of the present invention may include an internal aqueous phase, an oleaginous phase, and an external aqueous phase. The internal aqueous phase and the external aqueous may be independently composed of water or an aqueous solution. The oleaginous phase may be composed of a hydrophobic liquid or a hydrophobic solution. Hereinafter, "water-in-oil-in-water multiple emulsion" may be referred to as "multiple emulsion."

In the present invention, the active component may be a drug or a microorganism. The drug may include, but is not limited to, a small molecule drug, a biological preparation, or a traditional Chinese medicine preparation. Preferably, the drug is soluble and stable in water.

There is no limitation to the type of microorganism used in the present invention. For example, the microorganism may be a bacterium, a fungus, an actinomycete, a protozoa, or an alga. In some embodiments, the microorganism may be one or more probiotics, such as *Lactobacillus acidophilus, Bifidobacterium species, Lactobacillus casei* (*L. casei*), *Lactobacillus reuteri, Bifidobacterium lactis, Bifidobacterium longum*, and any combination thereof.

In some embodiments, the internal aqueous phase comprises water and an excipient. The excipient used herein includes one or more that are suitable for water-in-oil emulsions. For example, the excipient may be hydroxypropyl methylcellulose (HPMC), carboxymethyl cellulose, sodium alginate, gelatin, gum Arabic, sodium caseinate, soy protein, or any combination thereof.

The internal aqueous phase may also optionally include one or more salts. Preferably, the salt is a physiologically acceptable salt, such as sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate, and dipotassium hydrogen phosphate.

In some embodiments, the internal aqueous phase may include, based on the total weight of the internal aqueous phase, about 3 wt % of gelatin and about 2 wt % of sodium chloride.

There is no limitation to the process of the present invention for mixing the active component and the internal aqueous. For example, the active component may be one or more microorganisms (e.g., probiotics), which may be in the form of dry powder or cultural medium-containing. In some embodiments, after being cultivated, the cultural medium of the microorganism may be removed through centrifugation, and the pellet obtained may then be resuspended in an equal volume (the same volume as the supernatant) of the internal aqueous phase to form a homogenized mixture.

The oleaginous phase as used herein may be any hydrophobic liquids which that are suitable for water-in-oil emulsions, such as vegetable oils or animal oils. For example, the oleaginous phase may include one or more vegetable oils, such as sunflower oil, soybean oil, olive oil, canola oil, linseed oil, palm oil, and any combination thereof.

The oleaginous phase may also optionally comprise one or more lipophilic surfactants, such as polyglycerol polyricinoleate (PGPR), lecithin, a sugar ester, an emulsifying wax, a polyglycerol fatty acid ester, a polysorbate, a monoglyceride, a diglyceride, and any combination thereof.

In some embodiments, the oleaginous phase comprises sunflower oil, and, based on the total weight of the oleaginous phase, about 8 wt % of PGPR.

When the homogenized mixture is mixed with the oleaginous phase, a preferred way is to add the homogenized mixture to the oleaginous phase. In a further preferred embodiment, to maintain the activity of the active component the mixing process is performed under a low temperature (e.g., from about 0° C. to about 10° C., preferably about 4° C.). For example, the oleaginous phase is slowly stirred in an ice cooling bath by a homogenizer, the homogenized mixture is continuously added to the oleaginous phase, and the stirring speed is then raised to, for example, about 12000 rpm for about 3 minutes to form a water-in-oil emulsion. In some embodiments, the homogenized mixture and the oleaginous phase are mixed at a volume ratio of about 1:1.5.

Whey protein is a mixture of proteins isolated from whey, which is a liquid by-product from cheese production. The whey protein may be composed of α-lactalbumin, β-lactoglobulin, serum albumin and immunoglobulins. As compared to the other forms of whey proteins, a whey protein concentrate (WPC) typically comprises less fat and cholesterol, but more lactose-formed carbohydrates. Furthermore, the total amount of proteins in a whey-protein concentrate may range from about 29 wt % to about 89 wt % based on the total weight of the whey-protein concentrate. In a preferred embodiment of the present invention, the whey-protein concentrate used may have, based on the total weight thereof, greater than about 80 wt % of proteins.

The modified starch, which is useful as one of the excipients of the external aqueous phase, may be any modified starch which can be used as a food additive. In some embodiments, the modified starch is octenyl succinate modified starch (starch sodium octenyl succinate (OSA starch)).

In some embodiments, the weight ratio of the whey-protein concentrate to the modified starch ranges from about 4:1 to about 1:4, such as from about 3:1 to about 1:3, or from about 2:1 to about 1:2. Preferably, the weight ratio of the whey-protein concentrate to the modified starch is about 2:1.

In some embodiments, the external aqueous phase may optionally comprise an additional excipient selected from the group consisting of HPMC, carboxymethyl cellulose, sodium alginate, gelatin, gum Arabic, sodium caseinate, soy protein, and any combination thereof. The additional excipient in the external aqueous phase may be the same as or different from the excipient in the internal aqueous phase.

When the additional excipient is sodium alginate, the additional excipient preferably is not in gelation form. That is, the sodium alginate is not gelled. Accordingly, the multiple emulsion preferably does not contain any divalent cations, such as $Ca^{2+}$ or $Mg^{2+}$, which may result in sodium alginate gelation.

In some embodiments, the additional excipient is HPMC. In some embodiments, the external aqueous phase comprises, based on the total weight of the excipients, about 55 wt % to about 70 wt % of the whey-protein concentrate, about 25 wt % to about 35 wt % of the modified starch, and about 1 wt % to about 10 wt % of the additional excipient. Preferably, the weight ratio between the whey protein concentrate, the modified starch and the additional excipient is 38:19:3. In some embodiments, the external aqueous phase includes, based on the total weight thereof, about 25 wt % of the excipient(s), e.g., the whey-protein concentrate, the modified starch, and the additional excipient.

Similar to the foregoing, when the water-in-oil emulsion is mixed with the external aqueous phase, the external aqueous phase is stirred at a low speed by a homogenizer, and the water-in-oil emulsion is then added to the external aqueous phase. The volume ratio of the water-in-oil emulsion added to the external water phase may be about 2:8. Then, the stirring speed may be raised to, for example, about 8,000 rpm for about 2 minutes to form a water-in-oil-in-water multiple emulsion.

The aforementioned method of the present invention can encapsulate the active component in the multilayer film structure of the water-in-oil-in-water multiple emulsion to improve the stability of the active component, and can achieve the effects of isolation, protection, taste masking, and controlled release. When the active ingredient is a microorganism, the survival rate thereof can also be improved.

In some embodiments, the water-in-oil-in-water multiple emulsion can be spray-dried to form a multiple emulsion powder. In an embodiment, the inlet temperature and the outlet temperature may be about 130° C. and about 80° C., respectively. Through the spray-drying process, the moisture in the water-in-oil-in-water multiple emulsion can be partially or completely removed so that the resultant multiple emulsion powder has improved stability for storage.

The present invention further provides for a composition manufactured by the aforementioned method. Accordingly, the composition may be the water-in-oil-in-water multiple emulsion or the spray-dried multiple emulsion powder described above.

The following Examples are given for the purpose of illustration only and are not intended to limit the scope of the present invention.

EXAMPLES

1. Materials

| Materials | Sources |
|---|---|
| Sunflower oil | STANDARD FOODS CORPORATION |
| PGPR | CHEN DING ENTERPRISES CO., LTD. |
| Gelatin | Sigma-Aldrich |
| WPC | Haolong Food Industry Co., Ltd. |
| OSA | SAME CHIANG CO., LTD. |
| HPMC | WEI MING PHARMACEUTICAL MFG. CO., LTD. |
| Sodium alginate | Sigma-Aldrich |
| Gum Arabic | HAN-SIENT TRADING CO., LTD. |
| MRS broth | Difco |
| Agar | Pronadisa |

2. Experimental Methods

Preparation of Water-in-Oil-in-Water Multiple Emulsions

Multiple emulsions were manufactured by a two-step emulsification method. An internal aqueous phase, an oleaginous phase and an external aqueous phase were individually prepared, and the components thereof are listed in the table below. The formulae of excipient in the external aqueous phase are as described in the "Results and Discussion" section.

| Internal aqueous phase (water) | 3 wt % gelatin |
|---|---|
|  | 2 wt % NaCl |
| Oleaginous phase (sunflower oil) | 8 wt % PGPR |
| External aqueous phase (water) | 25 wt % excipient |

*Lactobacillus casei* (*L. casei*) cultural broth was centrifuged at 6,000 rpm for 5 mins. The supernatant was discarded, and the pellet was resuspended in the same volume of the internal aqueous phase to form a homogenized mixture. Then, 1×volume of the homogenized mixture was added to 1.5×volumes of the oleaginous phase existing in a homogenizer stirred at a low speed. After the homogenized mixture being completely added, the stirring speed was then raised to 12,000 rpm for 3 mins to properly mix the homogenized mixture with the oleaginous phase to form a water-in-oil emulsion. The homogenization process was conducted in an ice cooling bath to prevent death of *L. casei*.

Two×volumes of the water-in-oil emulsion were added to 8×volumes of the external aqueous phase existing in a homogenizer stirred at a low speed. After the water-in-oil emulsion was completely added, the stirring speed was raised to 8,000 rpm for 2 mins to form a water-in-oil-in-water multiple emulsion.

Preparation of Multiple Emulsion Powder

The aforementioned *L. casei*-containing water-in-oil-in-water multiple emulsion was spray-dried with the inlet temperature at 130° C. and the outlet temperature at 80° C. to form multiple emulsion powder. The powder obtained was collected and weighed to calculate the recovery rate (recovery rate=weight of the powder collected/weight of the solid content before spray-drying). The survival rate of *L. casei* in the multiple emulsion powder was measured by spreading the multiple emulsion powder onto a culture plate. The "*L. casei*-containing multiple emulsion powder" used thereafter is also referred to as "probiotic-containing multiple emulsion dosage form" or "*L. casei*-containing multiple emulsion dosage form."

Animal Model

Prescreening-Test

In order to rapidly identify which multiple emulsion dosage form can provide a probiotic the best protection, changes of fecal probiotic counts of different formulations were determined.

Animal Test

Two-month old male ICR mice were assigned to the following treatment groups (10 mice per group): control group, blank emulsion treated group, probiotic-containing multiple emulsion dosage form treated groups, and non-formulated *L. casei* treated group. In the test, 10 mL/kg. bw of deionized water (control group), $1\times10^8$ cfu/kg. bw of each of probiotic-containing multiple emulsion dosage forms E1 to E7 (see Table 3 in the "Results and Discussion" section), and $1\times10^8$ cfu/kg. bw of non-formulated *L. casei* (i.e., the cultural broth of *L. casei*) were orally administered to the mice of the groups, respectively. The feces of the mice for probiotic analysis were collected the day before administration (Pre-D1), and the $7^{th}$ day (D7) and $14^{th}$ day (D14) after administration.

Normal Mouse Model

One specific probiotic-containing multiple emulsion dosage form selected based on the results of the prescreening test was used to evaluate its efficacy in the mouse gastrointestinal tract. In the test, the efficacies of non-formulated *L. casei* and microcapsulated *L. casei* were also determined.

Two-month old male ICR mice were assigned to the following treatment groups (10 mice per group): control group ($H_2O$), blank emulsion (containing only the excipients of E5 shown in Table 3 in the "Results and Discussion" section) treated group, blank microcapsule (containing microcapsules only) treated group, non-formulated *L. casei* (*L. casei* cultural broth) treated group, probiotic-containing multiple emulsion dosage form (*L. casei* formulated with E5) treated group, and microcapsulated *L. casei* (*L. casei* encapsulated in microcapsules) treated group. In the test, 10 mL/kg. bw of deionized water (control group), 10 mL/kg. bw of the blank emulsion, 10 mL/kg. bw of the blank microcapsule (containing an external aqueous phase composed of soy protein and sodium alginate in a ratio of 9:1), $1\times10^8$ cfu/kg. bw of the non-formulated *L. casei*, $1\times10^8$ cfu/kg. bw of the probiotic-containing multiple emulsion dosage form, and $1\times10^8$ cfu/kg. bw of the microcapsulated *L. casei* were orally administered to the mice of the groups, respectively, once a day for three weeks. The feces of the mice for probiotic analysis were collected the day before administration (Pre-D1), and the $3^{rd}$ day (D3), $7^{th}$ day (D7) and $14^{th}$ day (D14) after administration. The mice were sacrificed at the $21^{st}$ day (D21) after administration, and the small intestine and cecum were collected to determine the activities of intestinal digestive enzymes, and the amounts of microbiota in the cecum.

Antibiotic-Treating Model

To evaluate the effects of the tested substances on the gastrointestinal function of mice, the mice were administered with a broad-spectrum antibiotic before administration of the tested substances. (Reference: Yang, L. C., Lu, T. J., and Lin, W. C. The prebiotic arabinogalactan of *Anoectochilus formosanus* prevents ovariectomy-induced osteoporosis in mice. *J Func Food* October 5(4); 1642-53)

Two-month old male ICR mice were assigned to the following treatment groups (10 mice per group): NT group (NT-$H_2O$; not treated with antibiotic), control group ($H_2O$), blank emulsion treated group (Blank E5), blank microcapsule treated group (Blank Microcapsule), non-formulated *L. casei* (*L. casei* cultural broth) treated group, probiotic-containing multiple emulsion dosage form treated group (E5+*L. casei*), and microcapsulated *L. casei* treated group (Microcapsule+*L. casei*). Except for the NT group, a broad-spectrum antibiotic, streptomycin, was added to the drinking water of all the other groups for 7 days before administration of the tested substances. Then, 10 mL/kg. bw of deionized water (NT group and control group), 10 mL/kg. bw of Blank E5, 10 mL/kg. bw of Blank Microcapsule, $1\times10^8$ cfu/kg. bw of *L. casei* cultural broth, $1\times10^8$ cfu/kg. bw of E5+*L. casei*, and $1\times10^8$ cfu/kg. bw of Microcapsule+*L. casei* were orally administered to the mice of the groups, respectively, once a day for three weeks. The feces of the mice for probiotic analysis are collected the day before administration (Pre-D1), and the 3rd day (D3), $7^{th}$ day (D7) and 14th day (D14) after administration. The mice were sacrificed at the $21^{st}$ (D21) day after administration, and the small intestine and cecum were collected to determine the activities of intestinal digestive enzymes, and the amounts of microbiota in the cecum.

Intestinal Digestive Enzyme Analysis

The activities of digestive enzymes, including lipase, leucine amino peptidase, and disaccharidase, were measured as described below.

Sample Preparation

After sacrifice, a section of the small intestine of each mouse was collected to analyze the activities of leucine amino peptidase and disaccharidase, and the intestinal mucosa was collected to analyze the activity of lipase. 0.2 g of the small intestine or the intestinal mucosa was added to 2 mL of a solution containing protease inhibitors (1 M phenylmethylsulfonylfluoride (PMSF) and 2.2 mM iodoacetic acid) and 0.9% NaCl at 4° C., and then the solution was homogenized to form a small intestinal homogeneous solution or an intestinal mucosal homogeneous solution.

Disaccharidase Activity Test

The purpose of this test was to determine the activity of disaccharidase (maltase and sucrase) in the mouse small intestine.

The method used generally followed the protocols disclosed by Dahlqvist, A. (Method for assay of intestinal disaccharidase. *Anal. Biochem.* 1964 January; 7: 18-25). Briefly, 30 μL of the intestinal mucosal homogeneous solution was added to 15 μL of 56 mM disaccharide solution (containing lactose, maltose, or sucrose), and the mixture was reacted at 37° C. for 30 minutes. After the reaction, 100 μL of 0.6 N sodium hydroxide solution was added to the mixture to lyse the cells, and then 10 μL of 6 N hydrochloric acid solution was added to neutralize the treated intestinal mucosal homogeneous solution. 45 μL of the neutralized intestinal mucosal homogeneous solution and 45 μL of each of different glucose standard solutions at concentrations from 0 to 40 mg/mL were independently mixed with 625 μL of reaction buffer (50 mM Tris-maleate, 33 mM potassium sodium phosphate, and 30 mM $MgCl_2$, pH 6.8), 150 μL of 1 mM ATP, 150 μL of 1 mM NADP, 15 μL of 330 IU/mL hexokinase (EC 2.7.1.11), and 15 μL of 170 IU/mL Glucose-6-phosphate dehydrogenase (EC 1.1.1.49), and the obtained mixtures were allowed to be reacted at 37° C. for 30 minutes. The reaction was stopped by disposing the mixtures in an ice cooling bath. At the beginning of the reaction, absorbance A1 was measured at a wavelength of 340 nm, and after 30 minutes of reaction, absorbance A2 was measured. The increased amount of NADPH, $^\Delta A=A2-A1$, was used to calculate the concentration of glucose (referring to the instructions of Randox GL 1611 reagent kit). The contents of proteins in the reacted mixtures were determined by the modified Lowry method (Peterson, G. L. (1977) A simplification of the protein assay method of Lowry et al. which is more generally applicable. Anal. Biochem. 83:346-356), and the activity of disaccharidase was presented as IU/mg protein.

Lipase Activity Test

The purpose of this test was to determine the activity of lipase in the mouse small intestine.

The method used generally followed the protocols disclosed by Verduin, P A et al. (Studies of the determination of lipase activity. Clin Chim Acta. 1973 Jun. 14; 46(1):11-9). Briefly, the activity of lipase was measured by using a commercial kit (Sigma Lipase-PS™). 900 μL of the substrate solution (containing 1.1 mM 1,2-diglyceride, 2 mM N-ethyl-N-(2-hydroxy-3-sulfopropyl)-sodium metaformate, 0.66 mM ATP, 860 U/L monoglyceride lipolytic enzyme, 1340 U/L glycerol kinase, 40,000 U/L 3-phosphate glycerol oxidase, 1340 U/L horseradish peroxidase, 40,000 U/L colipase, and a buffer) was mixed with 15 μL of the small intestine homogeneous solution and a standard solution (provided in Sigma Lipase-PS™), respectively, and the obtained mixtures were reacted at 37° C. for 3 to 5 minutes. Then, 300 μL of the activator (containing 36 mM deoxycholic acid, 6 mM 4-aminoantipyrine, 0.05% sodium azide, and a buffer solution) was added to each of the mixtures to further react at 37° C. for 3 to 5 minutes. The reacted mixtures were then detected by a spectrophotometer at a wavelength of 550 nm for 2 minutes, and the contents of proteins in the reacted mixtures were determined by the modified Lowry method. The activity of lipase was presented as KU/mg protein.

Leucine Aminopeptidase Activity Test

The purpose of this test was to determine the activity of protein digestive enzyme on the brush border of the small intestinal villi.

The method used generally followed the protocols disclosed by Martinek, P G et al. (Simplified estimation of leucine aminopeptidase (LAP) activity. Clin. Chem. 1964 December; 10: 1087-97). Briefly, the activity of leucine aminopeptidase was measured by using a commercial kit (Sigma Diagnostics® LAP). 0.5 mL of the intestinal mucosal homogeneous solution was mixed and reacted with 0.5 mL LAP substrate solution (20 mg/dL L-leucyl-β-naphthylamine dissolved in phosphate buffer, pH 7.1) at 37° C. for 1 hour, and then 0.5 mL of 2 N HCl was added to reaction. 1.5 mL of the reacted intestinal mucosa mixture and 1.5 mL of standard solution (0-12 Sigma unit/mL) were respectively mixed and reacted with 0.5 mL of sodium nitrite solution at room temperature for 3 minutes, and the mixtures were further mixed and reacted with 1.0 mL of 0.5% (w/v) ammonium sulfamate at room temperature for 3 minutes. The treated mixtures were then mixed and reacted with 2.0 mL of N-1-naphthaleneethylenediamine alcohol solution at room temperature for 45 minutes. The absorbances of the final products at a wavelength of 580 nm were measured by a spectrophotometer, and the protein contents in the final products were determined by the modified Lowry method. The activity of the leucine aminopeptidase was presented as Sigma unit/mg protein. 1 Sigma unit is defined as the amount of enzyme that produces 1 mol naphthylamine per hour at 37° C. and pH 7.1.

Improvement shown in any of the above tests indicates that the function of gastrointestinal digestion is improved.

Cecal Microbiota and Fecal Microbiota Analysis

Fresh feces of mice collected at the time points set in the test were used to determine the amounts of the tested probiotics in the feces. After the mice were sacrificed, collected contents of the ceca were used to determine the amounts of microbiota in the ceca. The fecal/cecal microbiota analyses included determining the amounts of probiotics (including L. casei and Bifidobacteria) and one harmful (or non-beneficial) bacterium: Clostridium perfringens.

Sampling and Homogenization Methods

The fecal samples were collected by massaging the abdomens of the mice, and were individually stored in an airtight container (about 3 to 10 pieces). After being weighed, the fecal samples were individually added to a sterile anaerobic diluent (0.1% peptone solution) at a ratio of 1:9 (w/w), and were mixed and suspended to form fecal homogeneous solutions. After the feeding steps, the mice were anesthetized and dissected to collect the cecal contents. About 1 g of each of the cecal content samples was added to 9 mL of sterile anaerobic diluent in a test tube, and was mixed and suspended to form a homogeneous solution (referring to the protocols of "Gastrointestinal Function Improvement Evaluation of Healthy Food" DOH Food No. 88037803 announced on Aug. 2, 1999 and DOH Food 0920401629 amended on Aug. 29, 2003; and Yang, L. C., Lu, T. J., and Lin, W. C.; The prebiotic arabinogalactan of Anoectochilus formosanus prevents ovariectomy-induced osteoporosis in mice. J Func Food October 5(4); 1642-53).

In an anaerobic glove box, each fecal homogenous solution and each cecal homogeneous solution were serially 10-fold diluted to an appropriate concentration. Each appropriate dilution was spread on a culture plate (spread plate method) and incubated in an anaerobic glove box at 37° C. for 24 to 72 hours. The number of colonies grown on each plate was counted after incubation.

In this experiment, each probiotic was incubated in its selective culture medium.

According to ISO 7937 (2004 Microbiology of food and animal feeding stuffs—Horizontal method for the enumeration of Clostridium perfringens—Colony-count technique), Clostridium perfringens was incubated in tryptose sulfite cycloserine (TSC) agar culture medium.

If the number of probiotics in the cecal samples or fecal samples significantly increases, and if the number of Clostridium perfringens in the cecal samples or fecal samples decreases or does not significantly increase, it is considered that the tested substance has an intestinal microbiota improvement function.

Statistical Analysis

The experimental data were analyzed by one-way analysis of variance, and further analyzed by Dunnet or Duncan test. $P<0.05$ represents statistically significant.

3. Results and Discussion

Establishment of Multiple Emulsification System

In this experiment, *L. casei* was formulated with the external aqueous phases containing different excipients to form different oil-in-water-in-oil multiple emulsions by the aforementioned method. These oil-in-water-in-oil multiple emulsions were then spray-dried to obtain different *L. casei* products in powder form (i.e., multiple emulsion powders). This experiment was performed to evaluate the effect of a spray-dry process on the powder recovery rates and viable *L. casei* counts of different excipient formulations. The components in the external aqueous phases of the different excipient formulations are shown in Table 1 below. In Table 1 and hereinafter, whey protein concentrate is referred to as "WPC," and octenyl succinate modified starch is referred to as "modified starch" or "OSA."

As shown in Table 1, the powder recovery rate is poor (less than 10%) in the group having the external aqueous phase containing only the whey protein concentrate (WPC group). When the whey protein concentrate is combined with the modified starch (WPC:OSA groups), the powder recovery rate improves. As can be seen from Table 1, the *L. casei* counts of WPC group and WPC:OSA=2:1 group are higher, and the survival rates of *L. casei* after the spray-dry process (survival rate=the *L. casei* count in the powder/the *L. casei* count before spray drying) are also higher in both groups (the *L. casei* counts decline less than 2 log CFU/g, and are greater than $6 \times 10^7$ CFU/g). After comparing the powder recovery rates and the *L. casei* counts, WPC:OSA=2:1 group was considered the best formulation and was used in the following experiments.

TABLE 1

*L. casei* Counts and Survival Rates, and Powder Recovery Rates of Different Excipient Formulations

| Excipients | *L. casei* Counts (cfu/g) | *L. casei* Survival Rates (%) | Powder Recovery Rates (%) |
|---|---|---|---|
| WPC | 6.00E+07 | 3.8 | 6.25 |
| WPC:OSA = 2:1 | 6.48E+07 | 3.2 | 28.8 |
| WPC:OSA = 1:1 | 5.38E+06 | 0.22 | 32.0 |
| WPC:OSA = 1:2 | 5.20E+06 | 0.38 | 24.2 |
| OSA | 2.23E+07 | 1.5 | 25.4 |

Different additional excipients were used to substitute 5% of the total weight of the excipients in the external aqueous phase of WPC:OSA=2:1 (WPC:OSA:additional excipient=38:19:3) to obtain different multiple emulsion powders to evaluate the effects of the different additional excipients (shown in Table 2 below) on the recovery rates and the *L. casei* counts of the multiple emulsion powders obtained.

As shown in Table 2, the powder recovery rate of the group using only whey protein concentrate and modified starch (WPC:OSA=2:1 group) and those of the groups with 5% of the total weight of the excipients replaced with different additional excipients range from about 20% to about 32%. The groups respectively using HPMC and sodium alginate as the additional excipient (i.e., WPC:OSA:HPMC=38:19:3 group and WPC:OSA:Na-alginate=38:19:3 group) have *L. casei* counts up to $9 \times 10^7$ CFU/g and $8 \times 10^7$ CFU/g, respectively. The group using HPMC as the additional excipient (WPC:OSA:HPMC=38:19:3 group) has the best *L. casei* survival rate (7.5%), and the group using gelatin as the additional excipient (WPC:OSA:gelatin=38:19:3 group) has the second best *L. casei* survival rate (5.8%). This represents that said groups can provide a better protection effect to *L. casei* during the spray-dry process. Since many groups can provide a certain protection effect to *L. casei* during the spray-drying process to improve recovery rate, the groups with *L. casei* counts higher than $10^7$ CFU/g were used for further tests.

TABLE 2

*L. casei* Counts, Survival Rates, and Powder Recovery Rates of Different Excipient Formulations

| Excipients | *L. casei* Counts (cfu/g) | *L. casei* Survival Rates (%) | Powder Recovery Rates (%) |
|---|---|---|---|
| WPC:OSA = 2:1 | 6.48E+07 | 3.2 | 28.8 |
| WPC:OSA:HPMC = 38:19:3 | 9.17E+07 | 7.5 | 19.9 |
| WPC:OSA:Na-alginate = 38:19:3 | 8.10E+07 | 4.4 | 26.5 |

TABLE 2-continued

L. casei Counts, Survival Rates, and Powder Recovery
Rates of Different Excipient Formulations

| Excipients | L. casei Counts (cfu/g) | L. casei Survival Rates (%) | Powder Recovery Rates (%) |
|---|---|---|---|
| WPC:OSA:gelatin = 38:19:3 | 6.95E+07 | 5.8 | 32.1 |
| WPC:OSA:gum Arabic = 38:19:3 | 5.22E+07 | 2.3 | 24.9 |

To investigate the stability of the multiple emulsion system for encapsulating L. casei (i.e., L. casei multiple emulsion powder), different multiple emulsion powders with different excipient formulations (as listed in Table 3) were kept at 4° C.; the results are shown in FIG. 1. The initial L. casei count in each group was greater than $10^7$ CFU/g, and the L. casei count was measured again after 14 days. The decreased amount of L. casei count of each group was less than 0.3 log cfu/g. The group with the lowest survival rate was the group having only modified starch as the excipient (OSA group), while its survival rate still remained higher than 50%. The L. casei count was further measured after 28 days. Compared with the initial L. casei count, the survival rate of the OSA group is 64%, and the survival rates of the other groups were all higher than 64%. After being kept at 4° C. for 28 days, the L. casei counts of all groups were higher than $2 \times 10^7$ CFU/g, indicating that the L. casei multiple emulsion powder of the present invention can provide high stability.

Figure 2A:
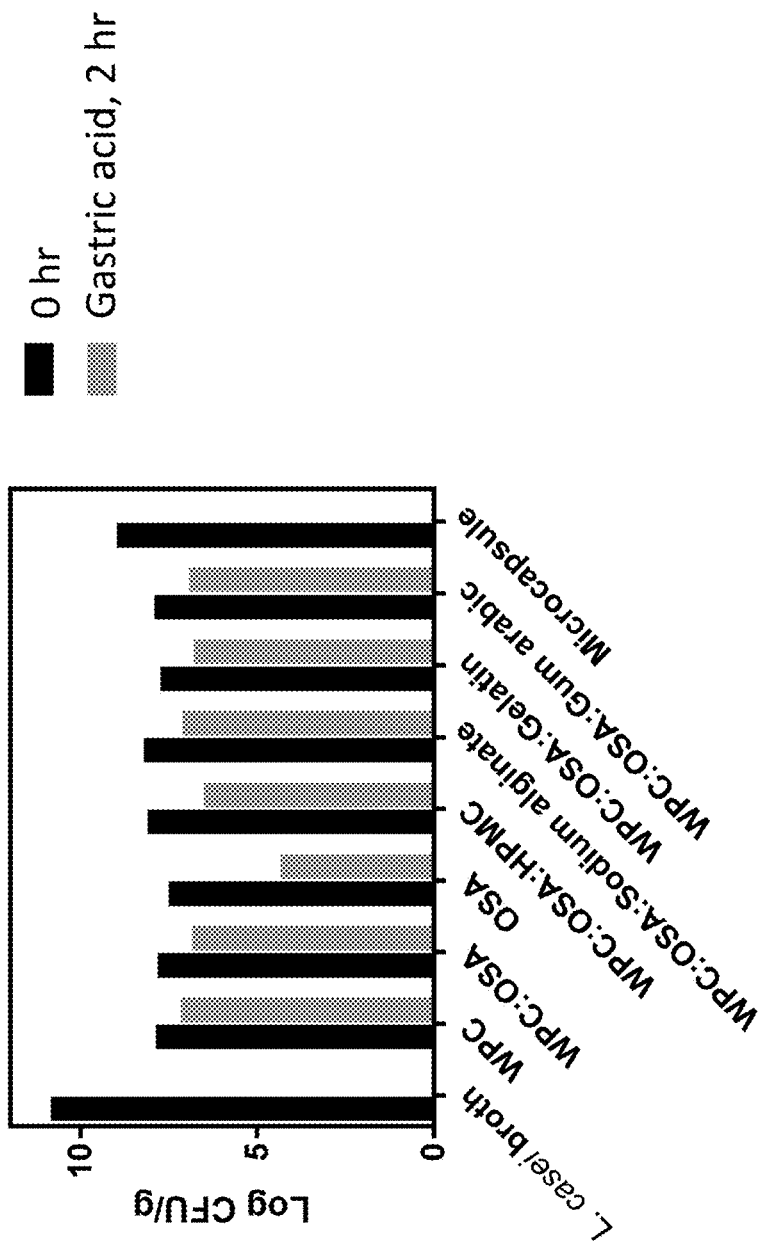
FIG. 2A shows the gastric acid resistance results of the rehydrated multiple emulsion powders.
Figure 2B:
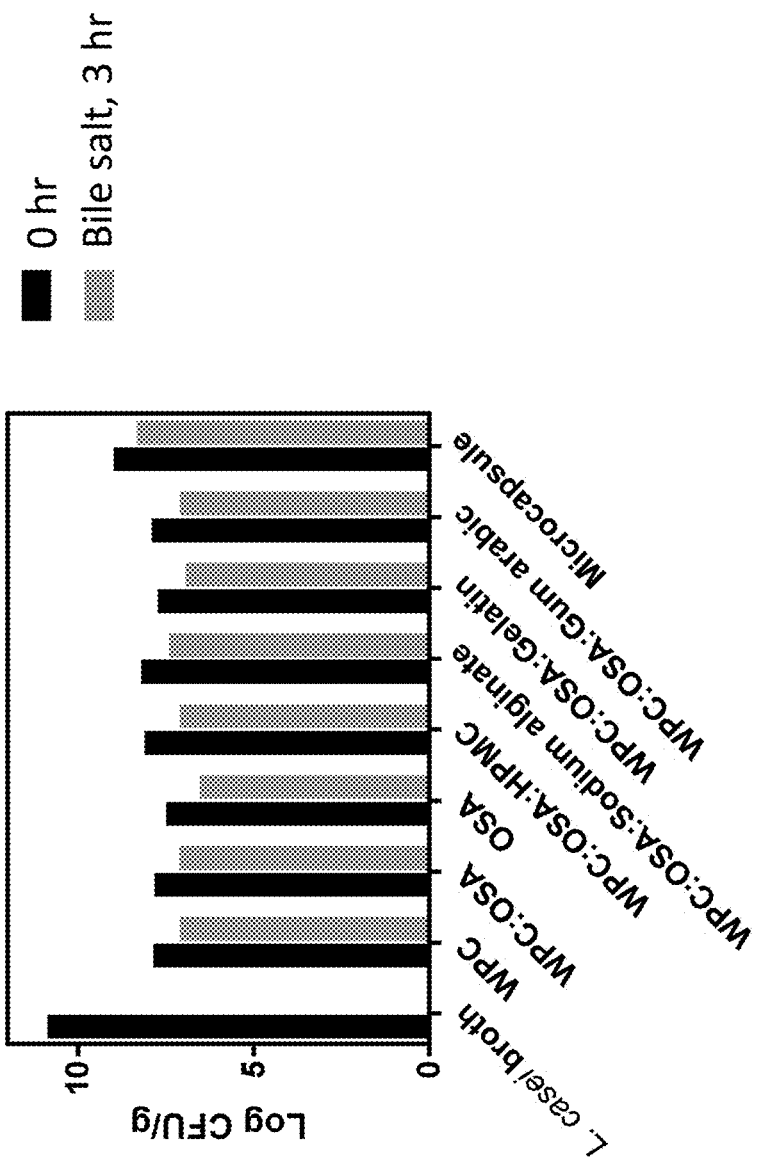
FIG. 2B shows the bile salts resistance results of the rehydrated multiple emulsion powders.

The L. casei multiple emulsion powders obtained above were rehydrated in water for tolerance analysis. Gastric acid and bile salt simulation solutions were respectively added to the rehydrated L. casei multiple emulsion solutions. After a predetermined period of time, the L. casei survival rate of each treated group was measured. The gastric acid tolerance results are shown in FIG. 2A. The reduction of L. casei counts of the different multiple emulsion rehydration groups with different formulations range from 0.7 log cfu/g to 3.2 log cfu/g. The bile salt tolerance results are shown in FIG. 2B. The reduction of L. casei counts of the multiple emulsion rehydration groups are all less than 1.0 log cfu/g. Compared with the non-encapsulated L. casei group (L. casei broth) and the microcapsulated L. casei group (Microcapsule+L. casei), the L. casei multiple emulsion powders of the present invention can provide a better protection effect. After being kept at 4° C. for 28 days, the L. casei counts in the multiple emulsion powders of the present invention were all greater than $2 \times 10^7$ CFU/g, indicating that the multiple emulsion powders of the present invention have a better powder stability.

Animal Test

Pre-Test

The mice were orally administered deionized water (Control), probiotic-encapsulating multiple emulsion powders E1 to E7 (the excipients in the external aqueous phases of the formulations are shown in Table 3 below), or non-encapsulated L. casei (L. casei broth) for 14 days. The feces of the mice were collected on the day before administration (Pre-D1), and the $7^{th}$ day (D7) and $14^{th}$ day (D14) after the administration. The feces collected were smeared on petri dishes. As shown in Table 4 below, the L. casei count of E5 group significantly increased on the $7^{th}$ day. On the $14^{th}$ day, as compared with the L. casei count of the control group, the L. casei count of the non-encapsulated L. casei group (L. casei broth) and those of E2 to E7 groups significantly increased. The increase of E5 to E7 groups were the highest.

TABLE 3

The Excipients in the External Aqueous Phases of the Formulations

| E1 | WPC |
| E2 | WPC:OSA = 2:1 |
| E3 | OSA |
| E4 | WPC:OSA:HPMC = 38:19:3 |
| E5 | WPC:OSA:Na-alginate = 38:19:3 |
| E6 | WPC:OSA:gelatin = 38:19:3 |
| E7 | WPC:OSA:gum Arabic = 38:19:3 |

TABLE 4

The L. casei Counts of the Feces of the
Mice Treated with Different Formulations

| Groups | Pre-D 1 (CFU/g) | D 7 (CFU/g) | D 14 (CFU/g) |
|---|---|---|---|
| Control | 7.41 ± 0.08 | 7.40 ± 0.20 | 7.52 ± 0.30 |
| L. casei broth | 7.45 ± 0.11 | 7.58 ± 0.11 | 7.94 ± 0.13* |
| E1 | 7.43 ± 0.11 | 7.60 ± 0.13 | 7.81 ± 0.13 |
| E2 | 7.49 ± 0.19 | 7.56 ± 0.11 | 7.99 ± 0.12* |
| E3 | 7.41 ± 0.08 | 7.60 ± 0.13 | 7.82 ± 0.36* |
| E4 | 7.40 ± 0.24 | 7.64 ± 0.16 | 7.90 ± 0.20* |
| E5 | 7.51 ± 0.22 | 7.70 ± 0.10* | 8.40 ± 0.09*** |
| E6 | 7.43 ± 0.15 | 7.58 ± 0.05 | 8.01 ± 0.12** |
| E7 | 7.49 ± 0.13 | 7.68 ± 0.17 | 8.18 ± 0.08*** |

*represents $p < 0.05$,
**represents $p < 0.01$, and
***represents $p < 0.001$.

Normal Mouse Model

Figure 3A:
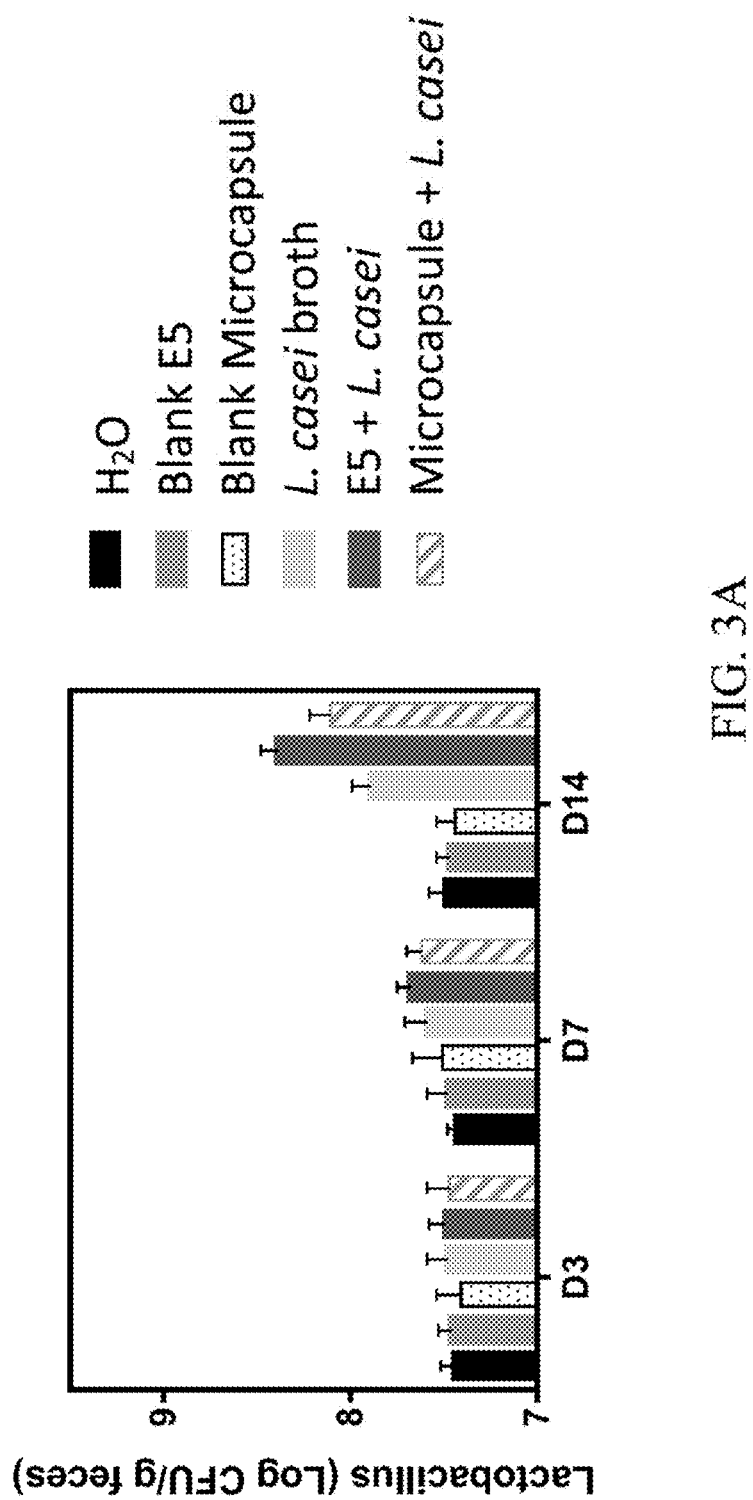
FIG. 3A shows the variations of the counts of *L. casei* in the feces of mice administered with the test substances over time (Day 3, Day 7, and Day 14).
Figure 3B:
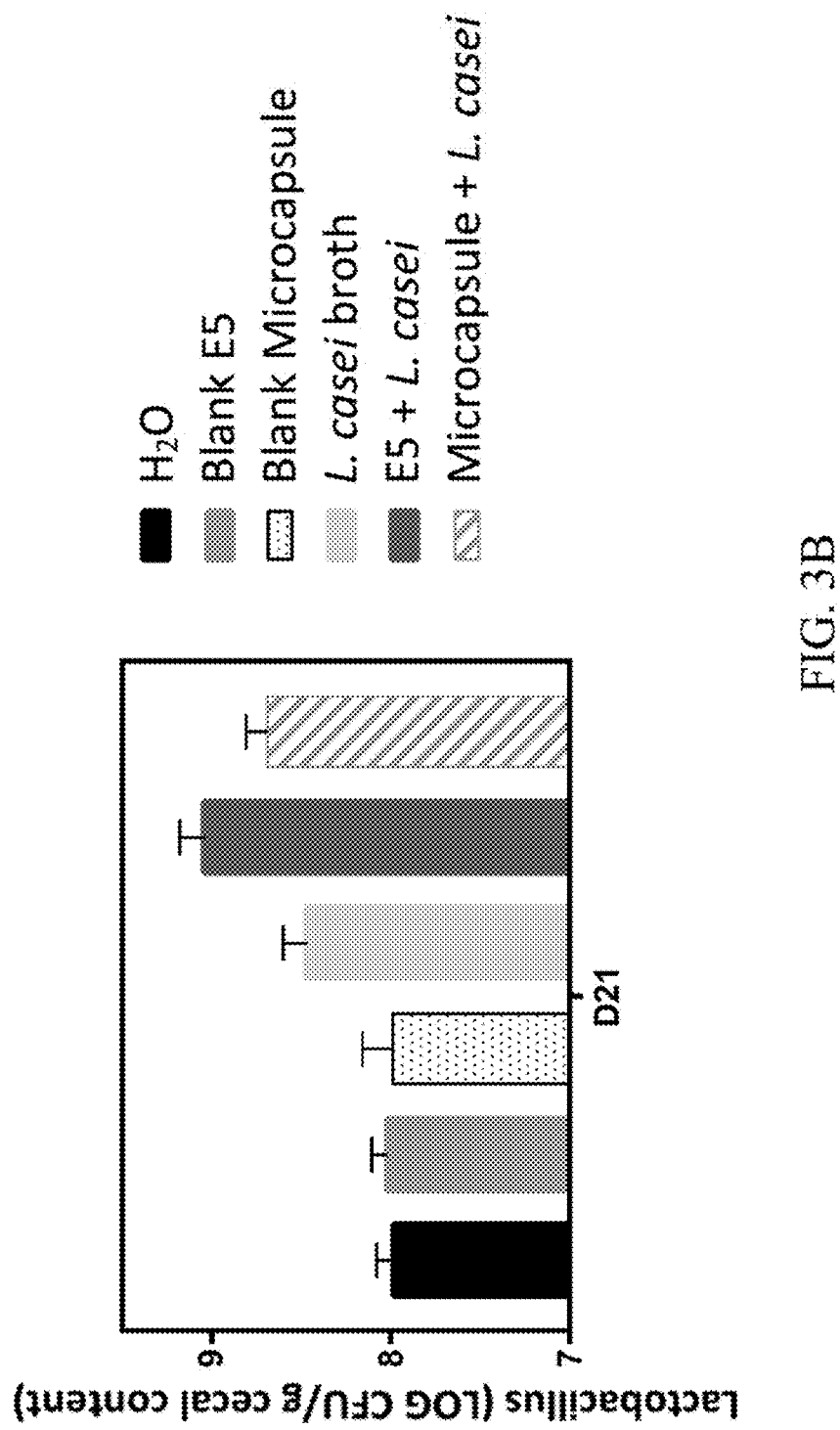
FIG. 3B shows the effects of the test substances on the amount of *L. casei* in the mouse cecal contents on Day 21.
Figure 4A:
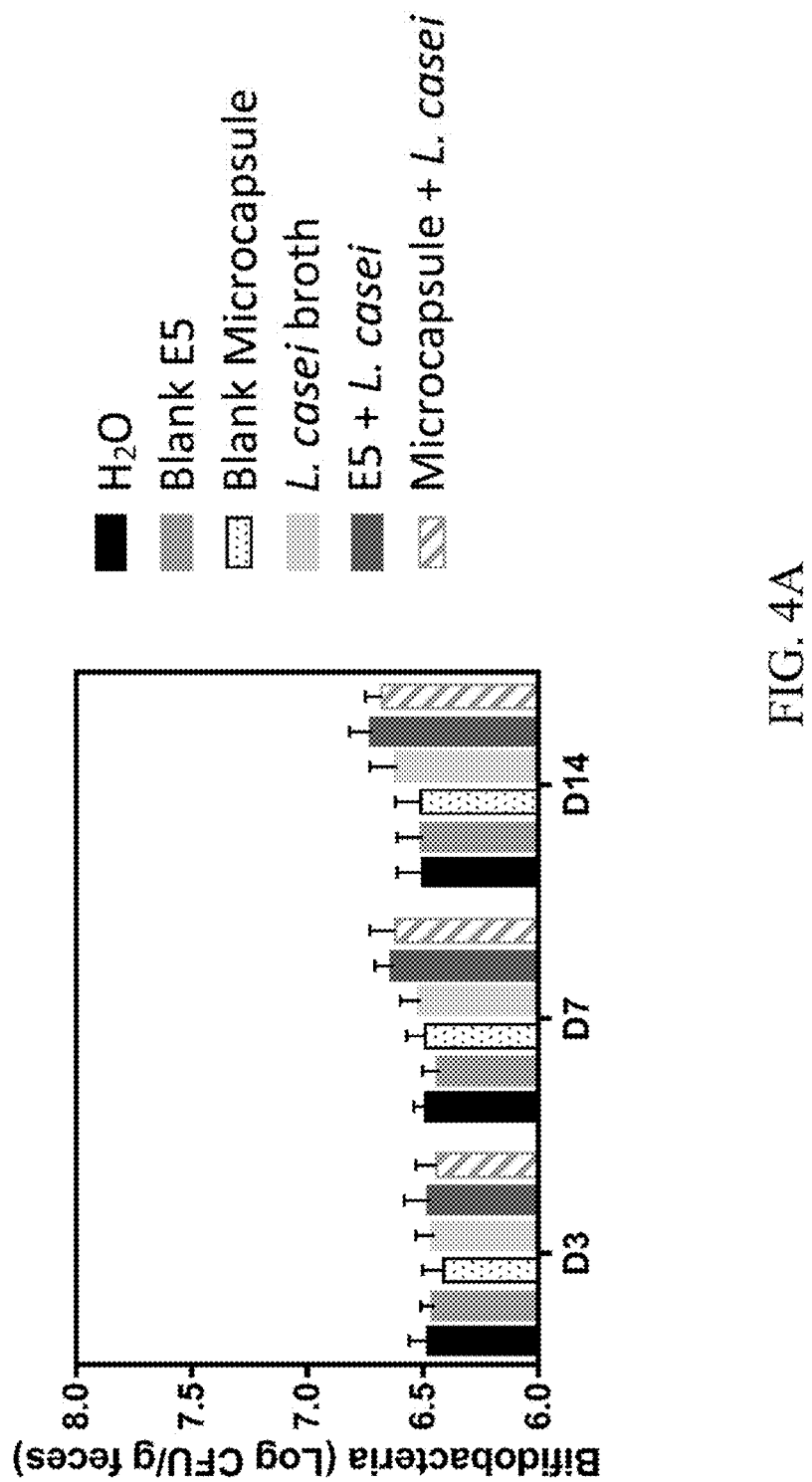
FIG. 4A shows the variations of the counts of Bifidobacteria in the feces of mice administered with the test substances over time (Day 3, Day 7, and Day 14).
Figure 4B:
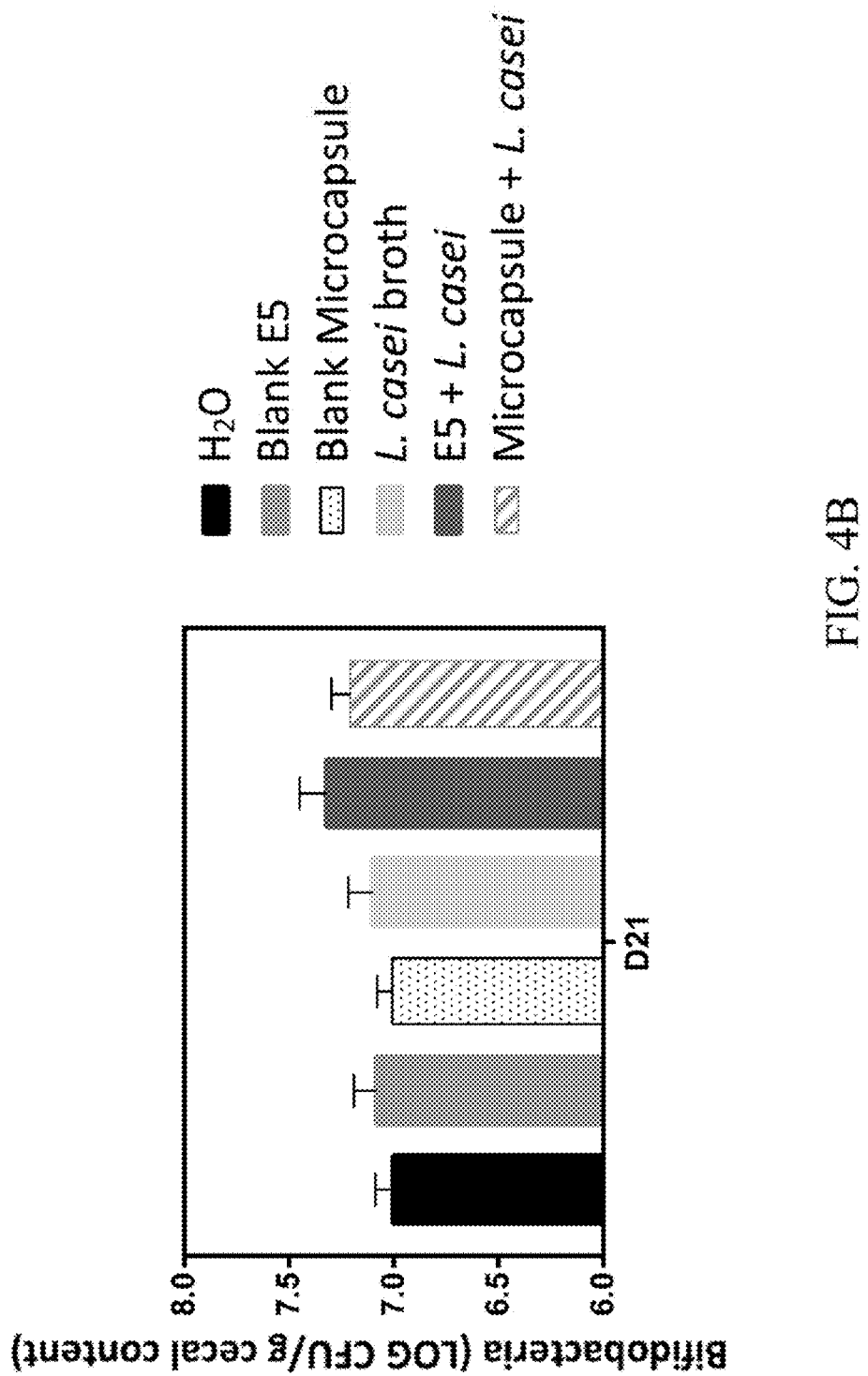
FIG. 4B shows the effects of the test substances on the amounts of Bifidobacteria in the cecal contents of mice administered with the test substance at the end of the tests (Day 21).
Figure 5A:
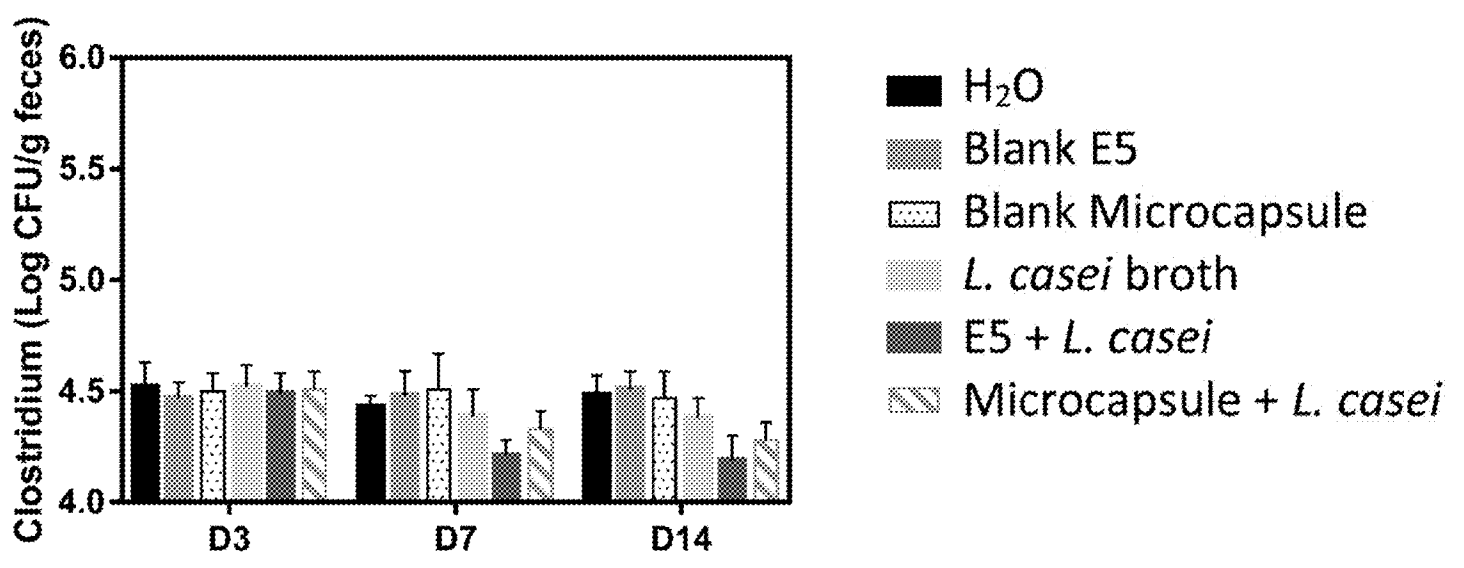
Figure 5B:
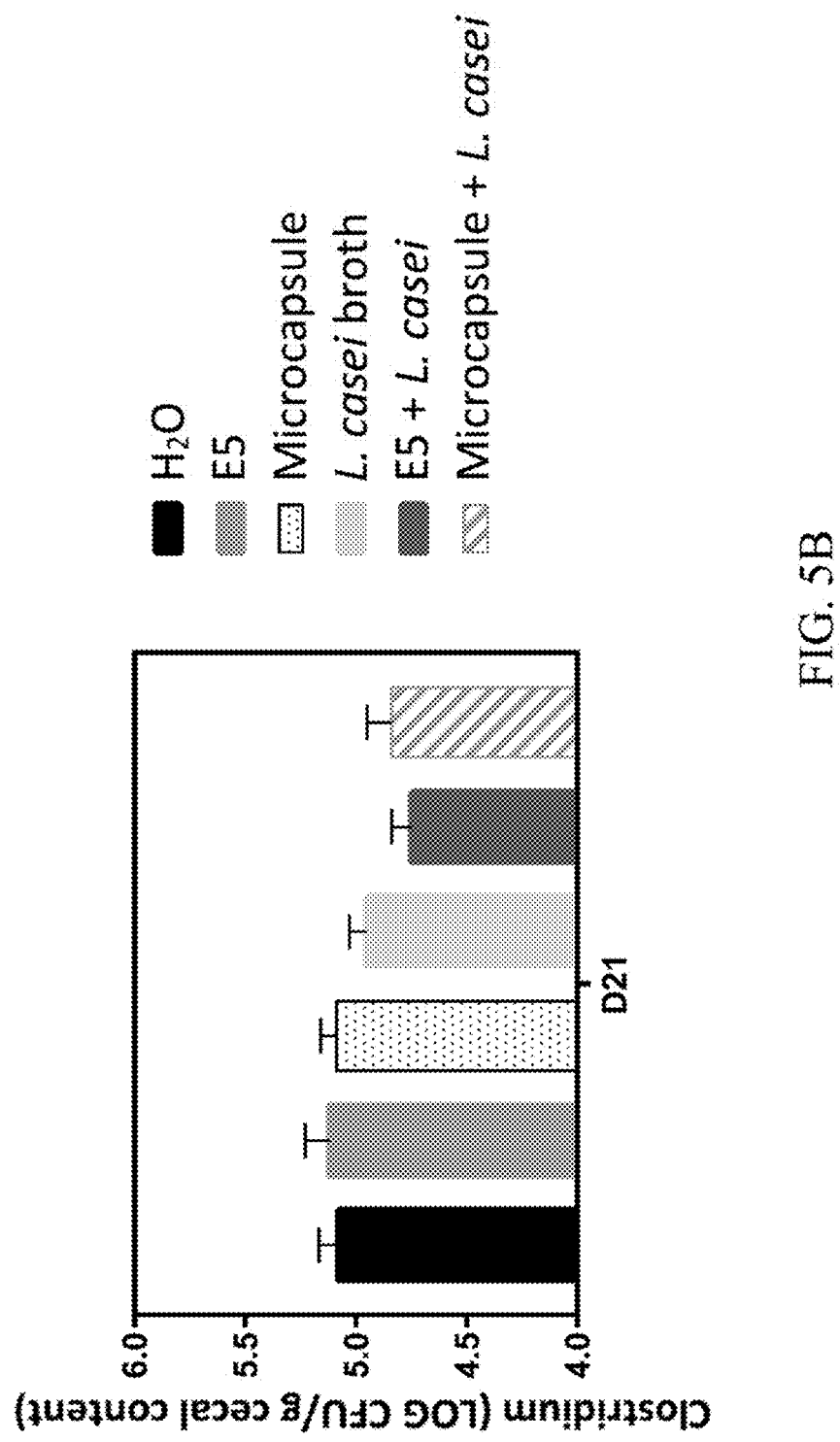
FIG. 5B shows the effects of the test substances on the amounts of *Clostridium perfringens* in the cecal contents of mice administered with the test substance at the end of the tests (Day 21).
Figure 6A:
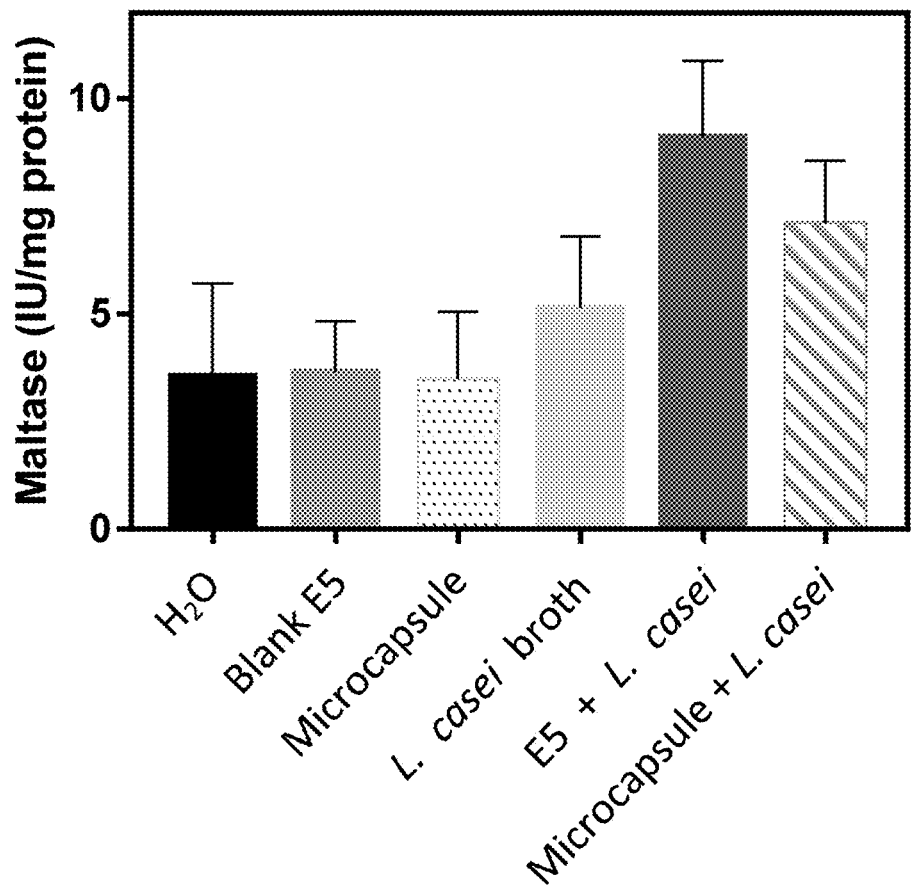
FIG. 6A shows the effects of the test substances on maltase activity in the intestines of mice administered with the test substance.
Figure 6B:
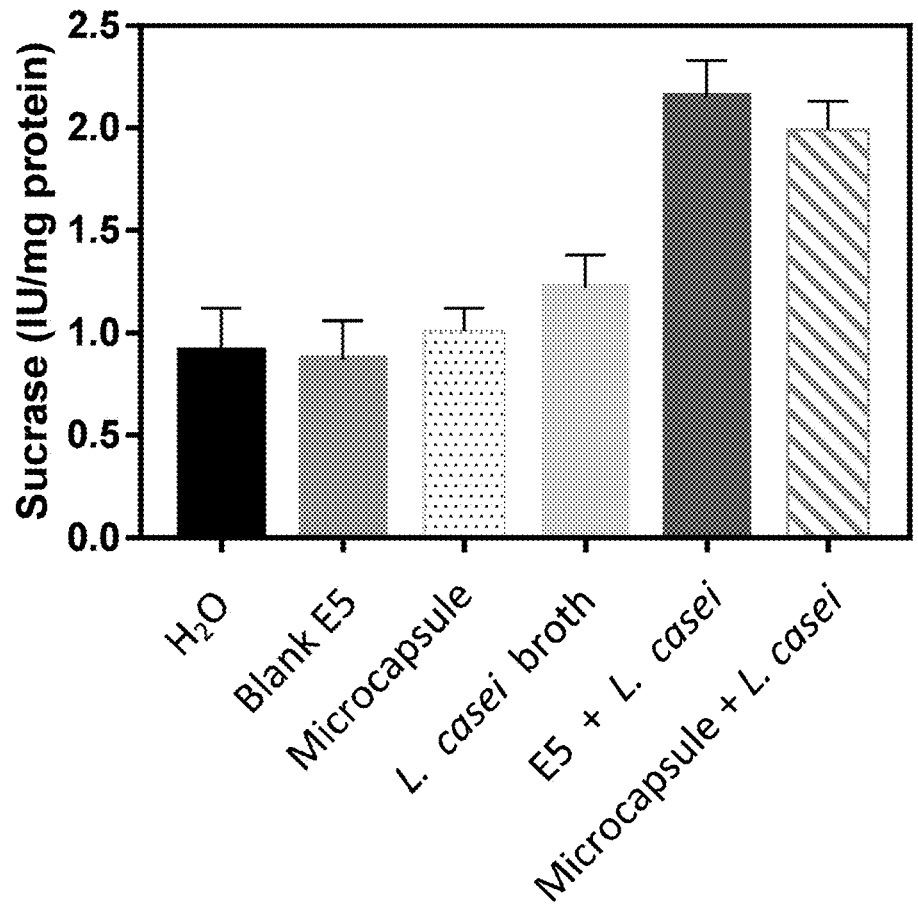
FIG. 6B shows the effects of the test substances on sucrase activity in the intestines of mice administered with the test substance.
Figure 6C:
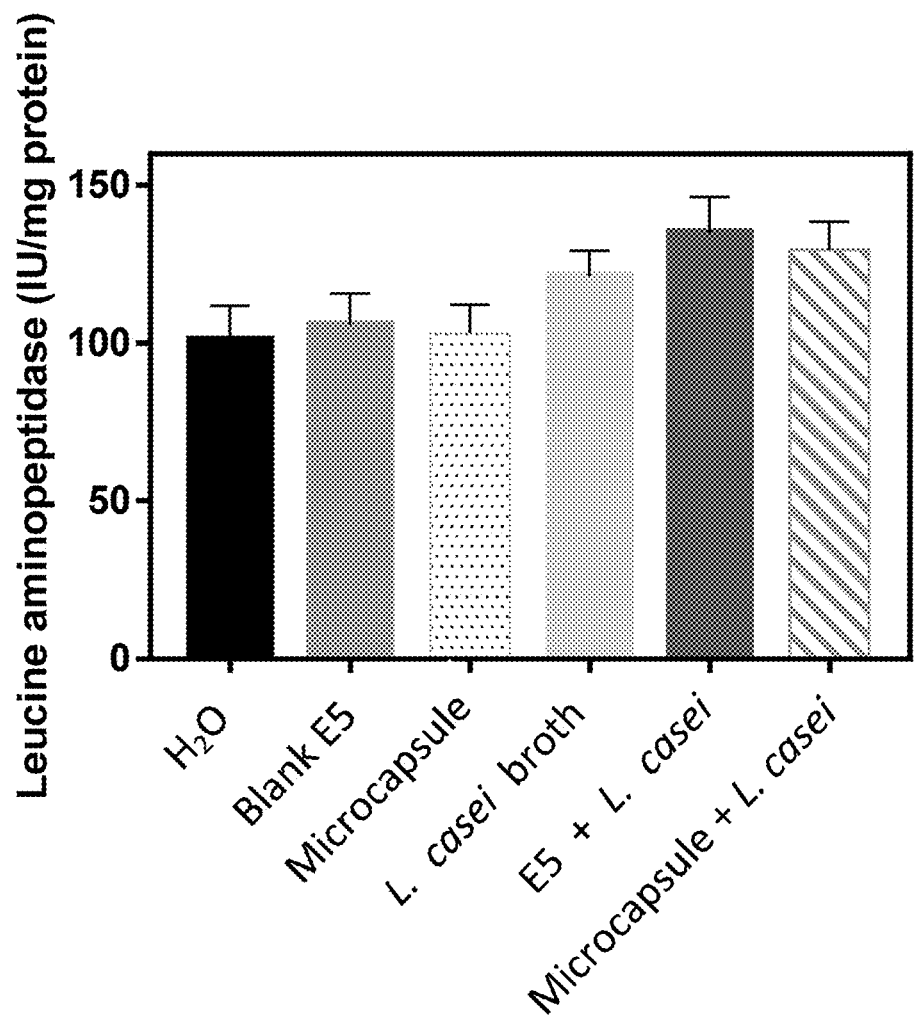
FIG. 6C shows the effects of the test substances on leucine aminopeptidase activity in the intestines of mice administered with the test substance.
Figure 6D:
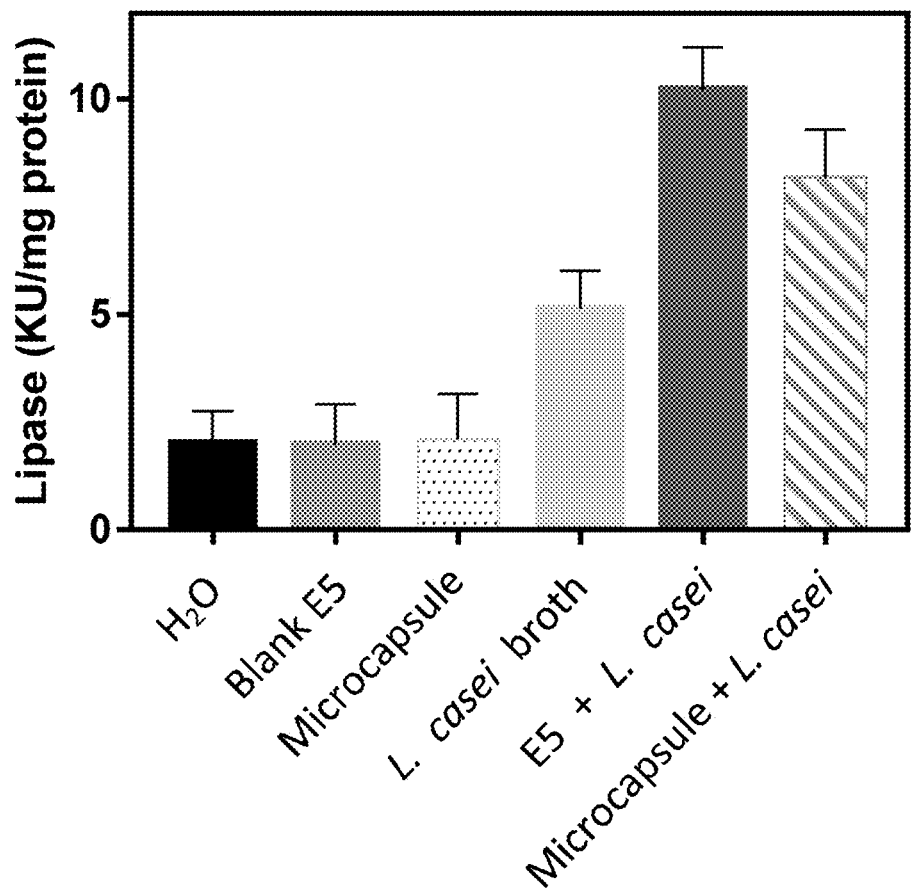
FIG. 6D shows the effects of the test substances on lipase activity in the intestines of mice administered with the test substance.

In a normal mouse model, the mice were administered with the tested substances for up to 3 weeks. No toxic reaction was observed during the experimental period. These test substances had no significant effect on the body weights of the mice. It was found that the L. casei counts of the feces (FIG. 3A) and cecal contents (FIG. 3B) of E5+L. casei group quickly and significantly increased, and the Bifidobacteria counts of the feces (FIG. 4A) and cecal contents (FIG. 4B) of E5+L. casei group also increased, but the Clostridium perfringens counts of the feces (FIG. 5A) and cecal contents (FIG. 5B) of E5+L. casei group decreased. It was also found that the excipient formulation of E5+L. casei group was able to increase the activities of intestinal maltase (FIG. 6A), sucrase (FIG. 6B), leucine aminopeptidase (FIG. 6C), and lipase (FIG. 6D).

As for the intestinal microbiota, it was found that the L. casei counts and Bifidobacteria counts of the mouse intestines of the groups respectively administered with L. casei-containing multiple emulsion powder (E5+L. casei) and L. casei-containing microcapsule (Microcapsule+L. casei) all increased, but only the L. casei-containing multiple emulsion powder (E5+L. casei) was able to significantly reduce the count of Clostridium perfringens (bad bacterium). The administration of the test substances improved the intestinal microbiota mainly due to the existence of L. casei. Since L. casei mainly colonizes in the small intestine rather than the cecum, it is believed that this may be the reason why the cecal contents were not affected by the test substances.

The *L. casei* used is a strain having starch degradation activity. Accordingly, the intestinal digestive enzyme activity tests show that administration of the *L. casei*-containing tested substances, including *L. casei* broth, *L. casei*-containing multiple emulsion powder (E5+*L. casei*) and *L. casei*-containing microcapsule (Microcapsule+*L. casei*), are able to increase the activity of disaccharidase in the intestinal mucosa, and the increased activity level shows positive correlation to the intestinal *L. casei* count. In addition, the group administered with the *L. casei*-containing multiple emulsion powder (E5+*L. casei*) shows the highest increasing level of the digestive enzyme activities, which indicates that the multiple emulsion powder of the present invention can significantly increase the *L. casei* count in the intestine.

Antibiotic-Treated Mouse Model

Figure 7A:
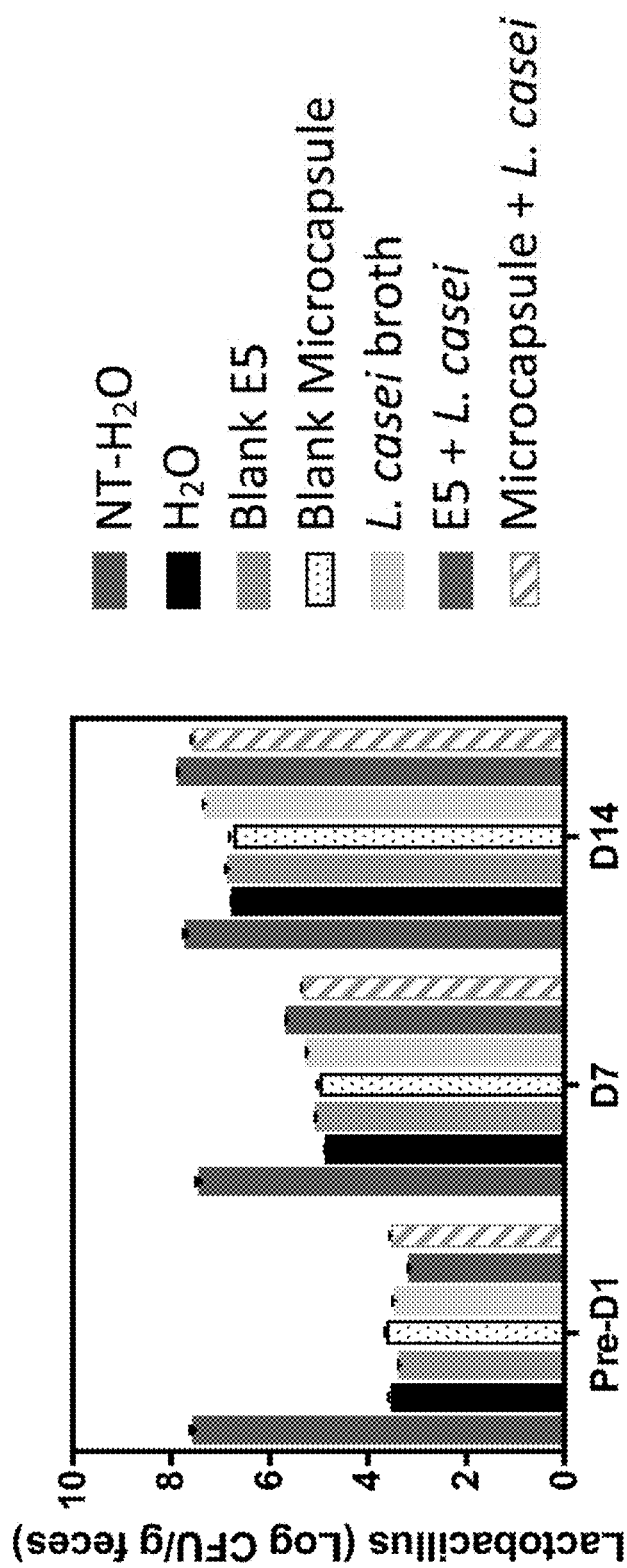
FIG. 7A shows the variations of the counts of *L. casei* in the feces of mice administered with the test substances over time (Pre-Day 1, Day 7, and Day 14).
Figure 7B:
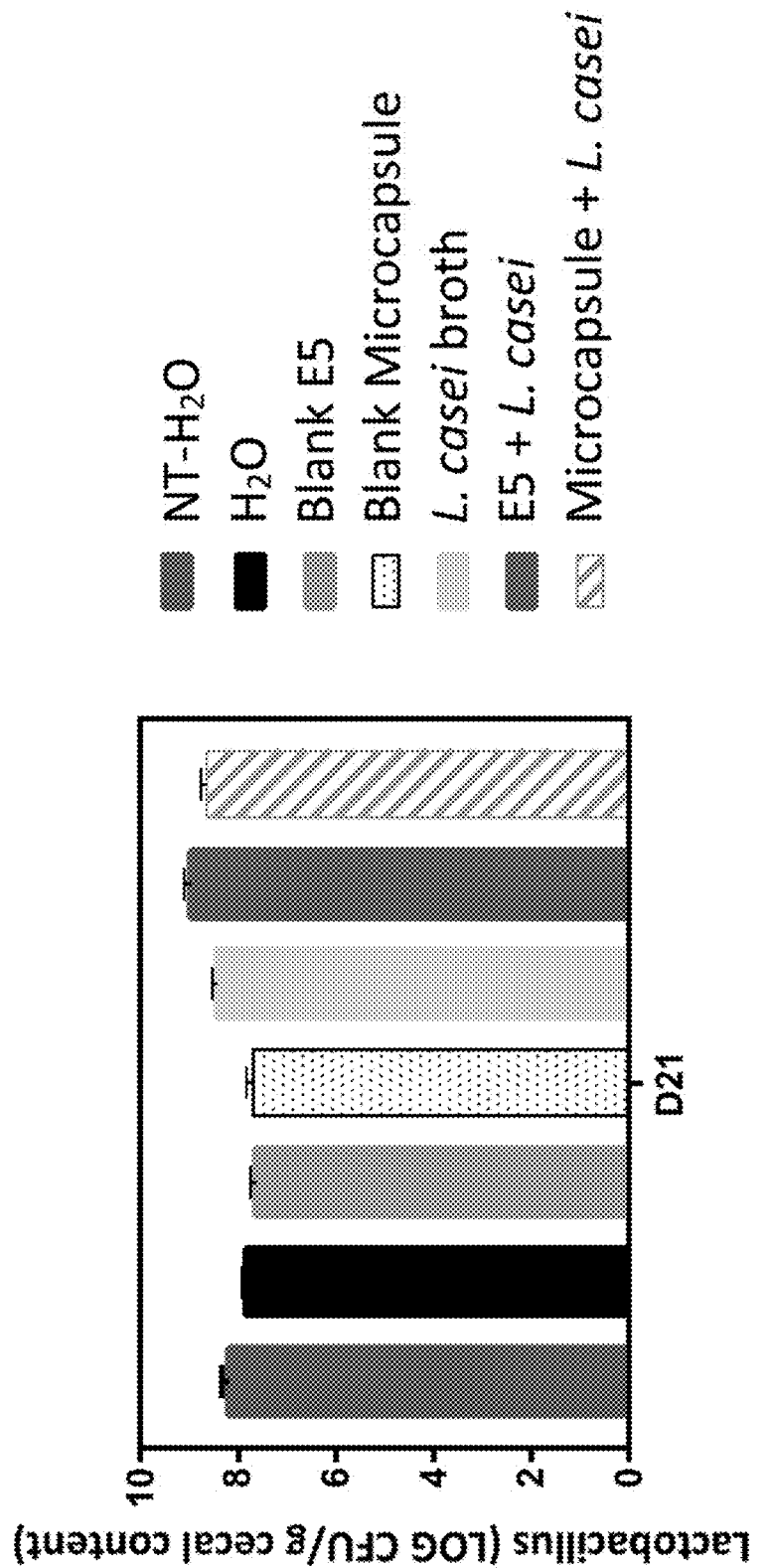
FIG. 7B shows the effects of the test substances on the amounts of *L. casei* in the cecal contents of mice administered with the test substance at the end of the tests (Day 21).
Figure 8A:
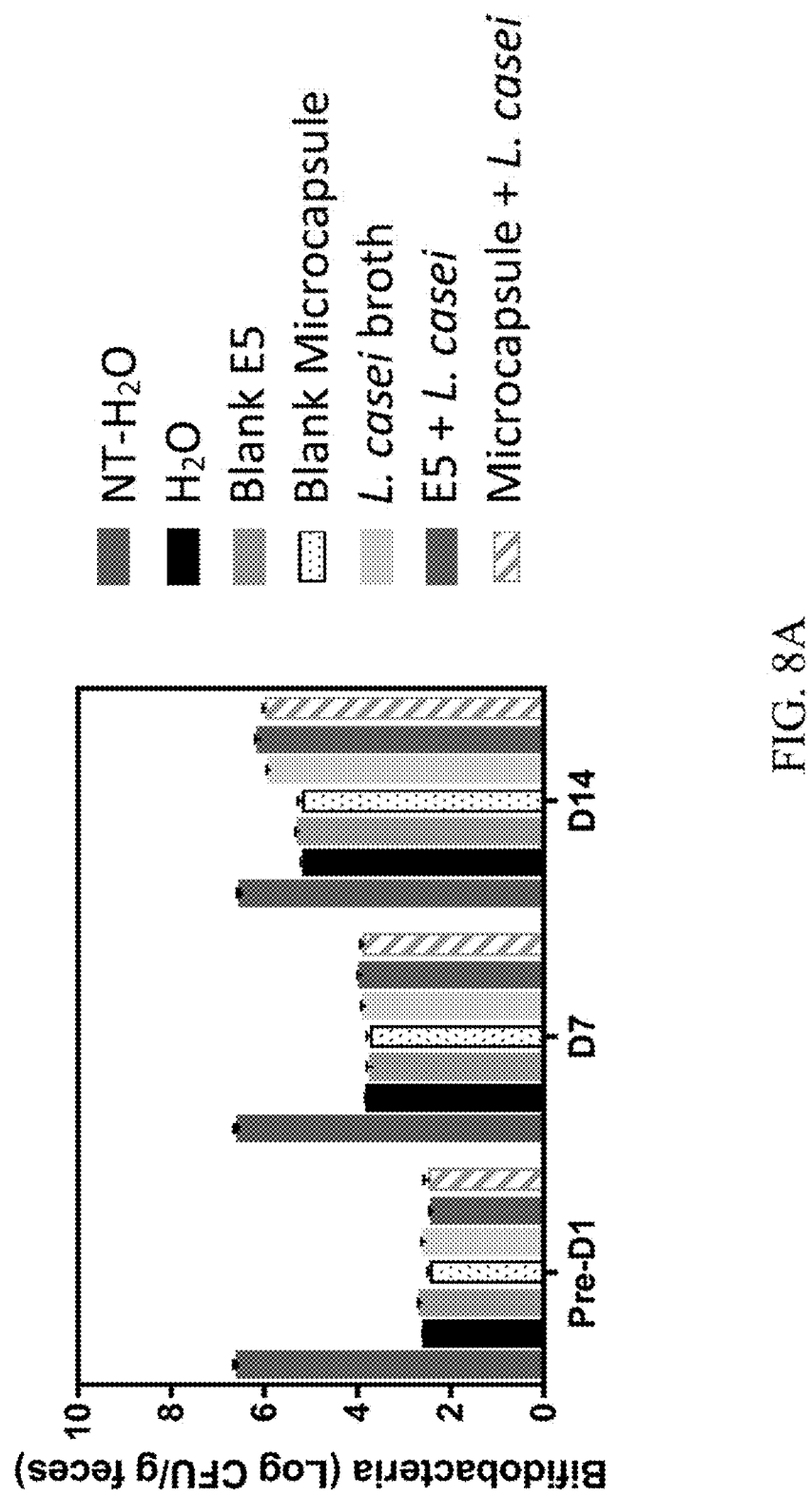
FIG. 8A shows the variations of the counts of Bifidobacteria in the feces of mice administered with the test substances over time (Pre-Day 1, Day 7, and Day 14).
Figure 8B:
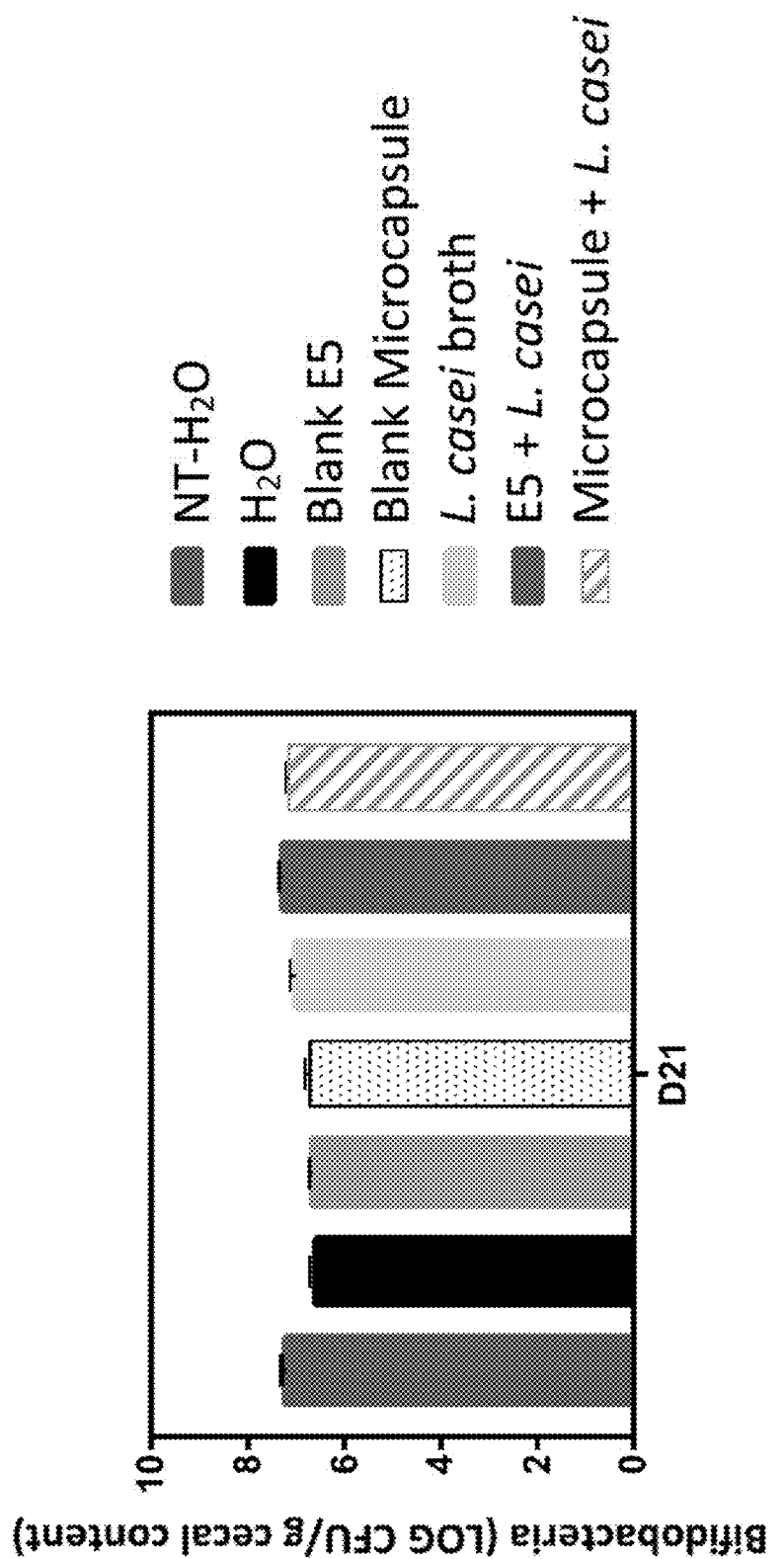
FIG. 8B shows the effects of the test substances on the amounts of Bifidobacteria in the cecal contents of mice administered with the test substance at the end of the tests (Day 21).
Figure 9A:
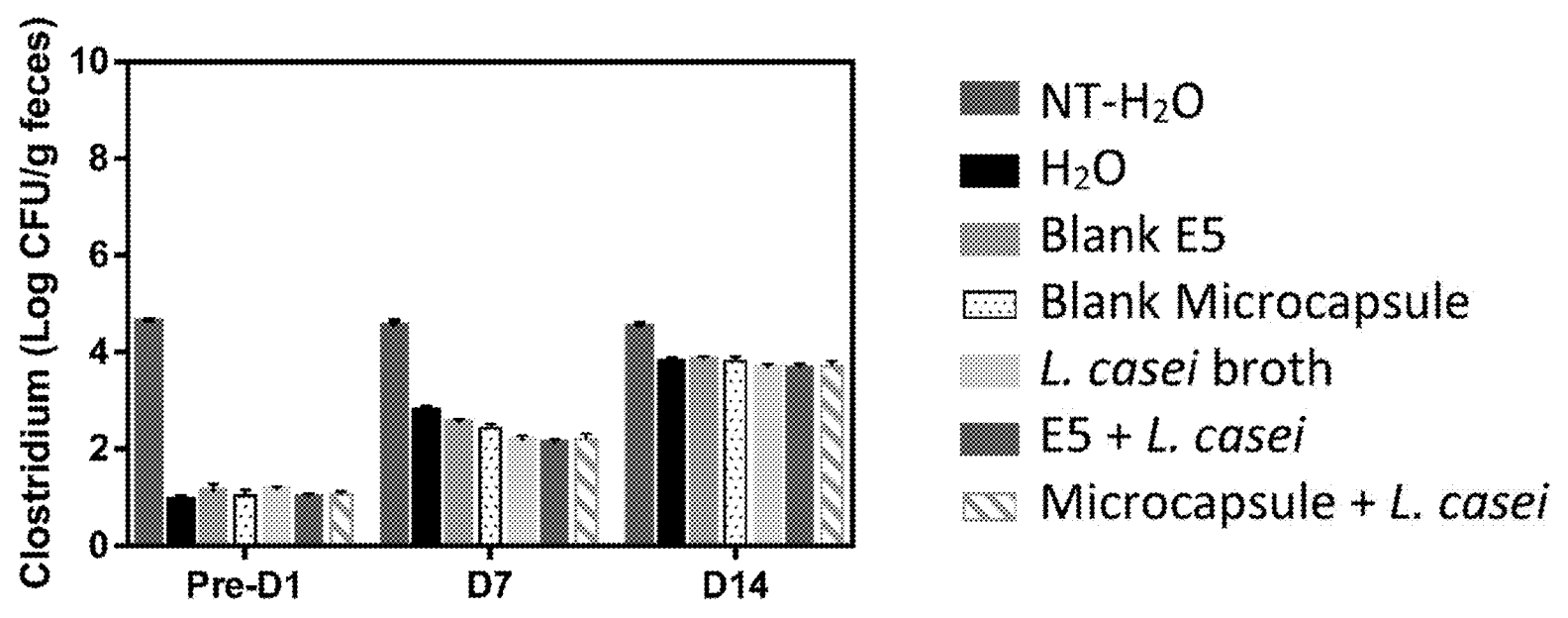
Figure 9B:
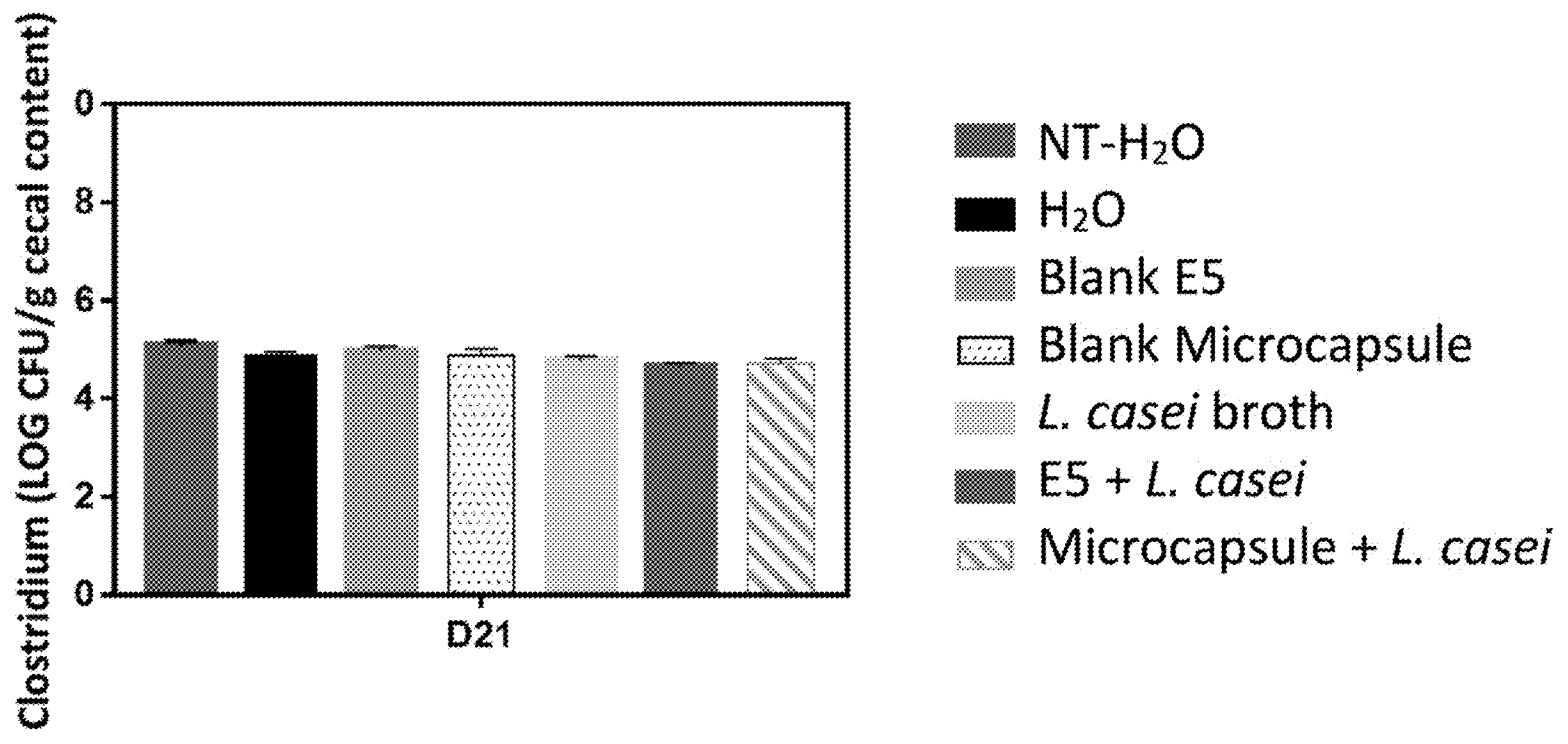
Figure 10A:
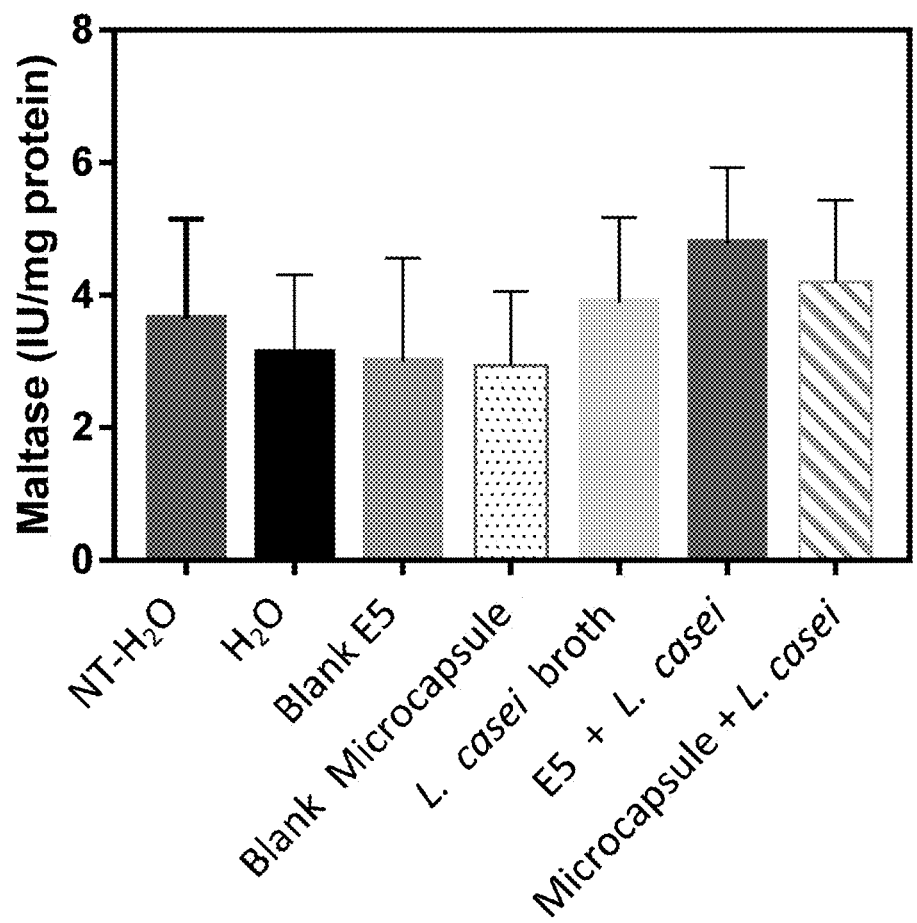
FIG. 10A shows the effects of the test substances on maltase activity in the intestines of mice administered with the test substance.
Figure 10B:
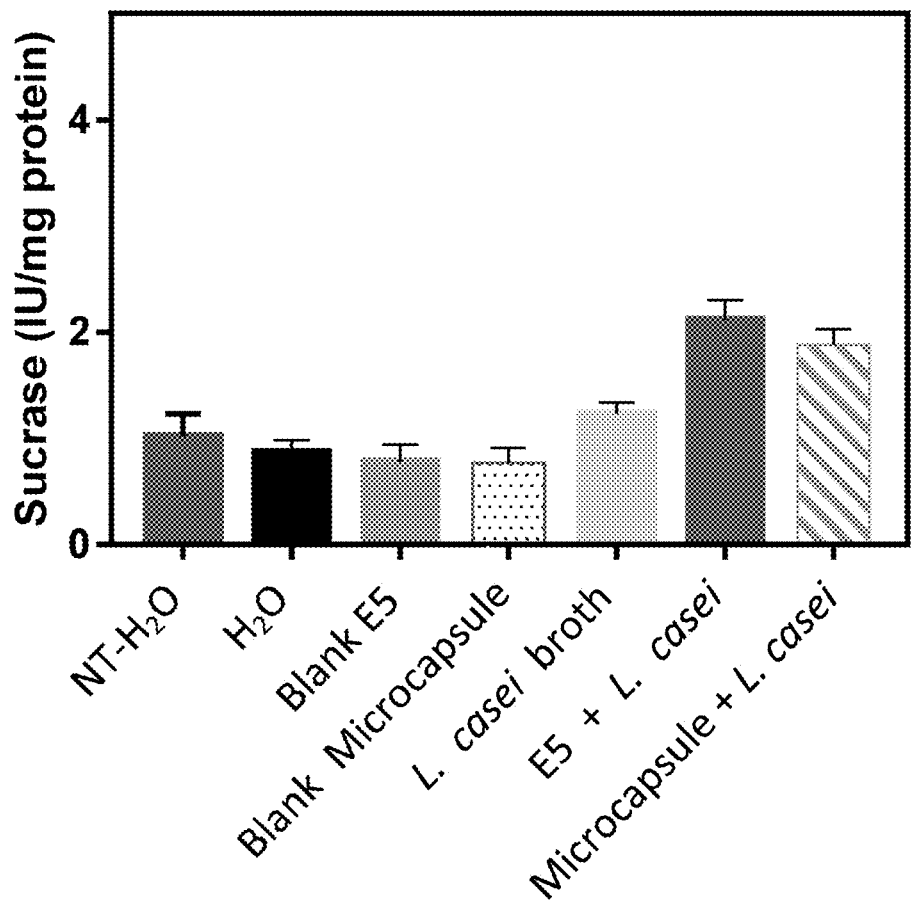
FIG. 10B shows the effects of the test substances on sucrase activity in the intestines of mice administered with the test substance.
Figure 10C:
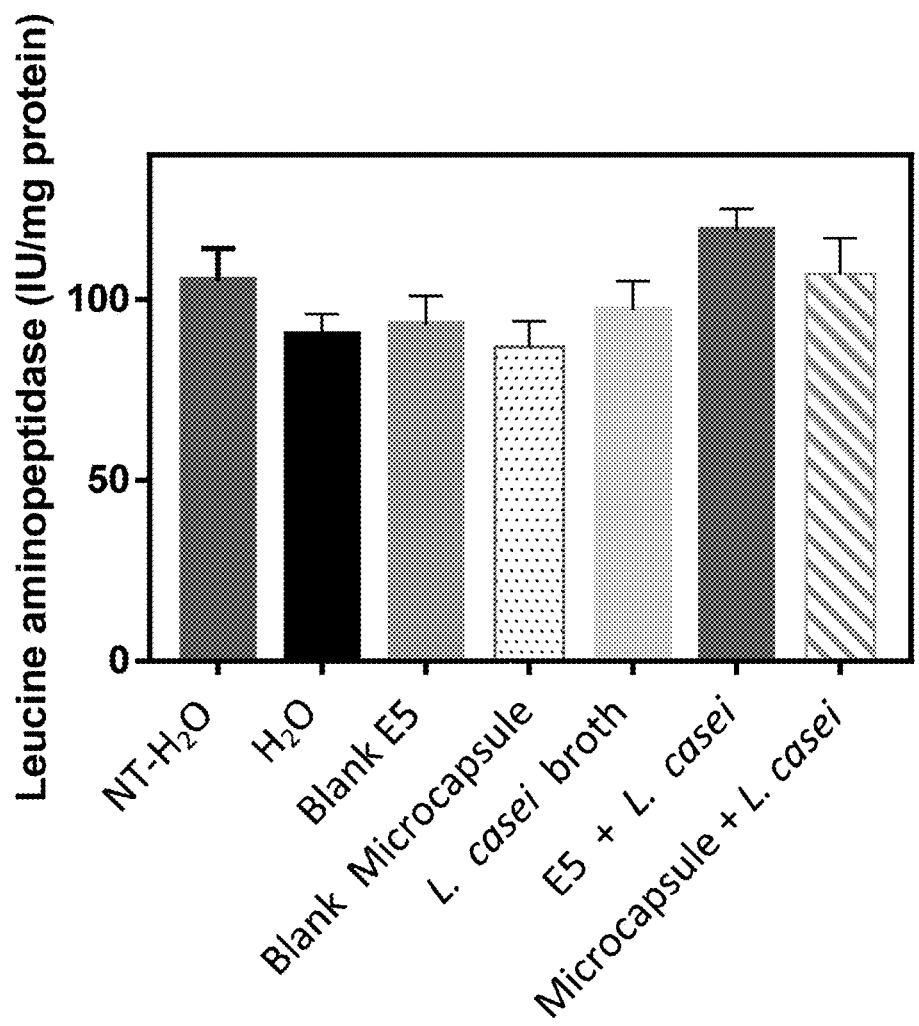
FIG. 10C shows the effects of the test substances on leucine aminopeptidase activity in the intestines of mice administered with the test substance.
Figure 10D:
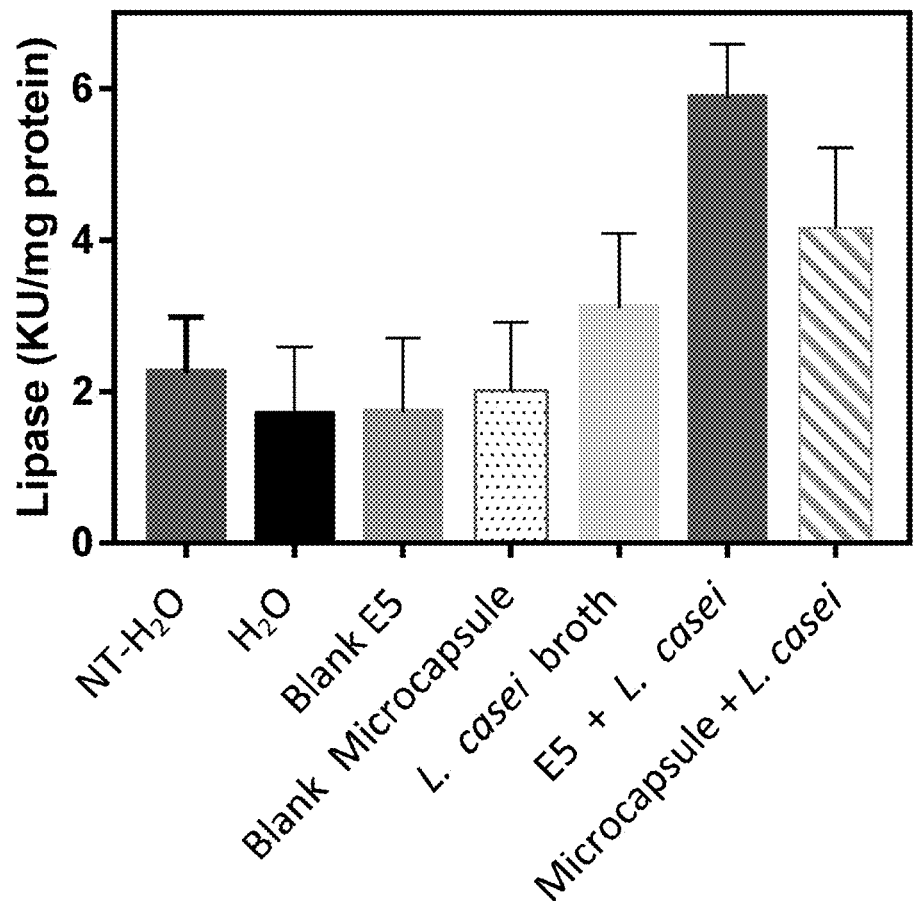
FIG. 10D shows the effects of the test substances on lipase activity in the intestines of mice administered with the test substance.

In the antibiotic-treated mouse model, the mice were administered with the tested substances after administration of a broad-spectrum antibiotic to reduce the amount of *Lactobacillus* in the feces. It was found that after the treatment with the tested substances, the *L. casei* counts of feces (FIG. 7A) and cecal contents (FIG. 7B) of E5+*L. casei* group quickly and significantly increased, and the Bifidobacteria counts of feces (FIG. 8A) and cecal contents (FIG. 8B) of E5+*L. casei* group also increased, but the *Clostridium perfringens* counts of feces (FIG. 9A) and cecal contents (FIG. 9B) of E5+*L. casei* group decreased. It was also found that the excipient formulation of E5+*L. casei* group was able to increase the activities of intestinal maltase (FIG. 10A), sucrase (FIG. 10B), leucine aminopeptidase (FIG. 10C), and lipase (FIG. 10D).

As shown in FIGS. 7 to 9, antibiotic treatment significantly reduced the counts of *Lactobacillus*, Bifidobacteria, and *Clostridium perfringens* in the mouse intestines. However, after the antibiotic treatment was stopped and the tested substances were administered, the counts of *Lactobacillus*, Bifidobacteria, and *Clostridium perfringens* all gradually recovered in Blank E5 group, Blank Microcapsule group and all the *L. casei*-containing groups (*L. casei* broth, E5+*L. casei*, and Microcapsule+*L. casei*). The recovery of the counts of intestinal *Lactobacillus* and Bifidobacteria of the group administered with *L. casei* encapsulated in the multiple emulsion powder (E5+*L. casei*) was higher than the other *L. casei*-containing groups, while the recovery of the counts of *Clostridium perfringens* of E5+*L. casei* group was slower. This is probably because the fast growth of probiotics in E5+*L. casei* group slows down the growth of *Clostridium perfringens*.

Stimulation of the growth of Bifidobacteria by the *L. casei*-containing multiple emulsion powder was observed in the antibiotic-treated mouse model, but such effect was not observed in the normal mouse model. This is probably because the antibiotic pre-treatment inhibits the growth of most bacteria (including Bifidobacteria) first, and the growth of Bifidobacteria can then be seen after the administration of the *L. casei*-containing multiple emulsion powder. Therefore, the *L. casei*-containing multiple emulsion powder of the present invention can improve the intestinal environment, and thus can promote not only the growth of *L. casei* but also the growth of the other probiotics, such as Bifidobacteria.

The results of intestinal enzyme activities show that the *L. casei*-containing multiple emulsion group (E5+*L. casei*) can increase the activities of disaccharidase, lipase, and leucine aminopeptidase. Such results correspond to the body weight change of the mice. During the intestinal enzyme analysis process, the body weights of the mice were recorded, as shown in Table 5. It can be seen from the table that after antibiotic treatment, the body weights of all mice decreased, and then gradually recovered. After administration of *L. casei*-containing multiple emulsion powder for 7 days, the body weights of the treated mice recovered to the same level as those of the mice of the NT group (not treated with antibiotic). According to such results, it can be assumed that *L. casei*-containing multiple emulsion powder of the present invention is able to improve the digestion and absorption of nutrients in the mouse intestine.

TABLE 5

Effects of Test Substances on Body Weights of Mice

| Groups | Antibiotic Treatment | Week 0 Weight (g) | Week 1 Weight (g) | Week 2 Weight (g) | Week 3 Weight (g) | Week 4 Weight (g) |
| --- | --- | --- | --- | --- | --- | --- |
| Deionized water | − | 34.5 ± 1.8 | 38.4 ± 1.1 | 39.7 ± 1.7 | 40.5 ± 1.8 | 40.8 ± 1.6 |
| Deionized water | + | 34.7 ± 1.1 | 36.0 ± 1.6 | 37.1 ± 2.1 | 37.6 ± 1.6 | 38.0 ± 1.3 |
| Multiple emulsion E5 | + | 34.4 ± 1.7 | 36.0 ± 1.8 | 37.3 ± 1.6 | 37.5 ± 1.5 | 38.9 ± 1.7 |
| Microcapsule | + | 34.8 ± 1.5 | 35.8 ± 1.4 | 37.0 ± 1.5 | 37.2 ± 2.1 | 38.8 ± 2.2 |
| *L. casei* broth | + | 34.3 ± 1.9 | 36.6 ± 1.8 | 37.7 ± 2.2 | 38.1 ± 1.9 | 38.6 ± 2.8 |
| Multiple emulsion E5 + *L. casei* | + | 34.6 ± 1.9 | 35.7 ± 1.9 | 38.7 ± 1.3 | 39.7 ± 1.2 | 40.6 ± 2.1 |
| Microcapsule + *L. casei* | + | 34.5 ± 1.6 | 36.3 ± 1.3 | 38.7 ± 1.5 | 38.9 ± 1.5 | 39.3 ± 1.1 |

The fecal and cecal smear tests can only analyze the count of *L. casei*; it cannot ascertain whether the increased amount of *L. casei* is due to the growth of *L. casei* originally living in the mouse intestine or the colonization of *L. casei* from the tested substances administered. Hence, quantitative real-time polymerase chain reaction (PCR) and *L. casei* specific primers were used to monitor the colonization of *L. casei* in the mouse intestine.

Figure 11A:
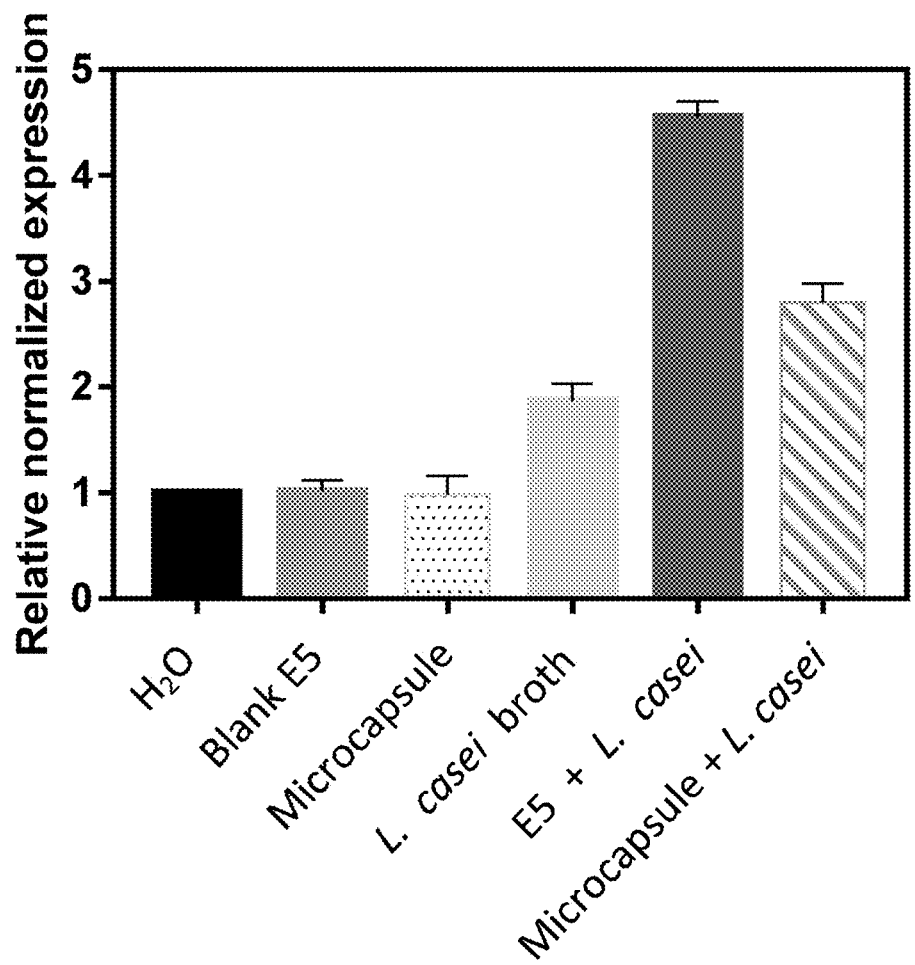
FIG. 11A shows the effects of the test substances on the expression of *L. casei* gene in the cecal contents of the normal mouse model administered with the test substance.
Figure 11B:
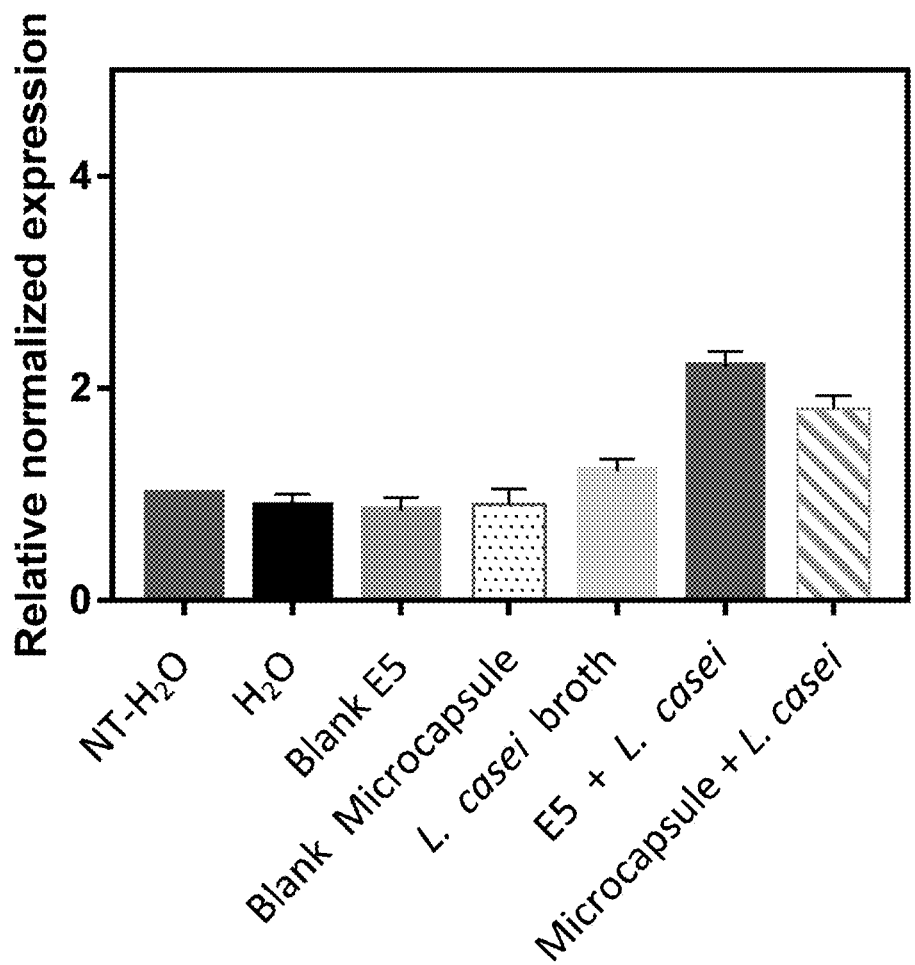
FIG. 11B shows the effects of the test substances on the expression of *L. casei* gene in the cecal contents of the antibiotic-treated mouse model administered with the test substance.

In the test, except for the mice of the blank emulsion groups and control groups, all the mice were administered with the same amount of *L. casei*. The PCR results are shown in FIG. 11A (normal mouse model) and FIG. 11B (antibiotic-treated mouse model). The results reveal that after administration, the administered *L. casei* cells were indeed colonized in the mouse intestine, and that the colonization of the *L. casei*-containing multiple emulsion group (E5+*L. casei*) and that of the microcapsulated *L. casei* group (Microcapsule+*L. casei*) were not only better than those of the blank emulsion groups and the control groups but also significantly better than that of the non-encapsulated *L. casei* group (*L. casei* broth). It is believed that the *L. casei*-containing multiple emulsion of the present invention is able to prevent a target substance (e.g., *L. casei*) from being destroyed by gastric acid and bile salt.

Through all of the above analyses and tests, it can be confirmed that the multiple emulsion powder of the present invention can indeed protect an active ingredient, such as probiotics (e.g., *L. casei*), to pass through the stomach, and thus enhance the physiological activity of the active ingredient in the gastrointestinal tract.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims.

What is claimed is:

1. A method for manufacturing a water-in-oil-in-water multiple emulsion, comprising:
    (a) mixing an active component with an internal aqueous phase to form a homogenized mixture;
    (b) mixing the homogenized mixture with an oleaginous phase to form a water-in-oil emulsion; and
    (c) mixing the water-in-oil emulsion with an external aqueous phase to form the water-in-oil-in-water multiple emulsion, wherein the external aqueous phase comprises water and an excipient, and wherein
        the excipient comprises a whey protein concentrate and a modified starch,
        the modified starch is octenyl succinate modified starch, and
        the weight ratio of the whey protein concentrate to the modified starch ranges from about 4:1 to about 1:4.

2. The method of claim 1, wherein the active component is a probiotic.

3. The method of claim 2, wherein the probiotic is selected from the group consisting of *Lactobacillus, Bifidobacterium*, and any combination thereof.

4. The method of claim 3, wherein *Lactobacillus* is selected from the group consisting of *Lactobacillus acidophilus, Lactobacillus casei*, and *Lactobacillus reuteri*.

5. The method of claim 3, wherein *Bifidobacterium* is selected from the group consisting of *Bifidobacterium lactis* and *Bifidobacterium longum*.

6. The method of claim 1, wherein the internal aqueous phase comprises water and an excipient.

7. The method of claim 6, wherein the excipient in the internal aqueous phase is selected from the group consisting of hydroxypropylmethylcellulose, carboxymethyl cellulose, sodium alginate, gelatin, gum Arabic, sodium caseinate, soy protein, and any combination thereof.

8. The method of claim 6, wherein the internal aqueous phase further comprises a salt.

9. The method of claim 8, wherein the salt is selected from the group consisting of sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate, dipotassium hydrogen phosphate, and any combination thereof.

10. The method of claim 1, wherein the oleaginous phase comprises a vegetable oil and a lipophilic surfactant.

11. The method of claim 10, wherein the vegetable oil is selected from the group consisting of sunflower oil, soybean oil, olive oil, canola oil, linseed oil, palm oil, and any combination thereof.

12. The method of claim 10, wherein the lipophilic surfactant is selected from the group consisting of polyglycerol polyricinoleate (PGPR), lecithin, sugar esters, emulsifying waxes polyglycerol fatty acid esters, polysorbates, monoglycerides, diglycerides, and any combination thereof.

13. The method of claim 1, wherein the weight ratio of the whey protein concentrate to the modified starch is about 2:1.

14. The method of claim 1, wherein the external aqueous phase further comprises an additional excipient selected from the group consisting of hydroxypropylmethylcellulose, carboxymethyl cellulose, sodium alginate, gelatin, gum Arabic, sodium caseinate, soy protein, and any combination thereof.

15. The method of claim 14, wherein the additional excipient is hydroxypropylmethylcellulose.

16. The method of claim 14, wherein the external aqueous phase comprises, based on the total weight of the excipients, about 55 wt % to about 70 wt % of the whey protein concentrate, about 25 wt % to about 35 wt % of the modified starch, and about 1 wt % to about 10 wt % of the additional excipient.

17. The method of claim 14, wherein the weight ratio between the whey protein concentrate, the modified starch and the additional excipient is 38:19:3.

18. The method of claim 1, which further comprises:
    (d) spray-drying the water-in-oil-in-water multiple emulsion to obtain a multi-emulsified powder.

19. A composition obtained by the method of claim 18.

20. A composition obtained by the method of claim 1.

* * * * *